(12) United States Patent
Stokes et al.

(10) Patent No.: US 9,333,001 B2
(45) Date of Patent: May 10, 2016

(54) ARTICULABLE LAPAROSCOPIC INSTRUMENT

(75) Inventors: Michael J. Stokes, Cincinnati, OH (US); Kempton K. Carroll, II, Cincinnati, OH (US); Christopher J. Hess, Cincinnati, OH (US); William B. Weisenburgh, II, Maineville, OH (US); Sean P. Conlon, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 686 days.

(21) Appl. No.: 12/876,300

(22) Filed: Sep. 7, 2010

(65) Prior Publication Data

US 2011/0087269 A1   Apr. 14, 2011

Related U.S. Application Data

(60) Provisional application No. 61/249,780, filed on Oct. 8, 2009.

(51) Int. Cl.
*A61B 17/00* (2006.01)
*A61B 17/29* (2006.01)
*A61B 17/34* (2006.01)

(52) U.S. Cl.
CPC ........... *A61B 17/29* (2013.01); *A61B 2017/292* (2013.01); *A61B 2017/2908* (2013.01); *A61B 2017/2922* (2013.01); *A61B 2017/3445* (2013.01)

(58) Field of Classification Search
CPC ......... G05G 11/00; G05G 1/00; A61B 1/005; A61B 1/0051; A61B 1/0058; A61B 1/008; A61B 1/01; A61B 19/2203; A61B 2019/2234; A61B 2019/2238; A61B 2017/2919; A61B 2017/2908
USPC ............. 606/205–208, 1, 139, 141–142, 167, 606/170, 159; 600/139, 141–142, 149; 294/111; 901/28, 15
See application file for complete search history.

(56) References Cited

U.S. PATENT DOCUMENTS 2,765,930 A   10/1956   Geer et al.
3,402,710 A   9/1968   Paleschuck
(Continued)

FOREIGN PATENT DOCUMENTS

DE   4300307 A1   7/1994
DE   4324254 C1   1/1995
(Continued)

OTHER PUBLICATIONS

"Applied GelPort Advanced Access Device," by Applied Medical Resources Corporation (Nov. 2002).
(Continued)

*Primary Examiner* — Amy R Weisberg
(74) *Attorney, Agent, or Firm* — Mintz Levin Cohn Ferris Glovsky and Popeo, P.C.

(57) ABSTRACT

A medical device comprises a handle comprises an actuator. A shaft extends distally from the handle. A first shaft segment extends proximally from the handle and has a proximal end and a distal end. A second shaft segment has a proximal end and a distal end and is pivotably supported with respect to the distal end of the first shaft segment at a position offset from a longitudinal axis of the shaft in a first offset direction. A third shaft segment has a proximal end and a distal end and is pivotably supported with respect to the distal end of the second shaft segment at a position offset from the longitudinal axis of the shaft in a second offset direction different from the first offset direction. A first member extends through at least a portion of the first shaft segment and is operatively associated with the actuator. A second member extends through at least a portion of the second shaft segment. The second member has a proximal end pivotably supported with respect to the distal end of the first member and a distal end pivotably supported with respect to the third shaft segment. The actuator is operative to provide substantially simultaneous compound articulation of the second and third shaft segments.

7 Claims, 21 Drawing Sheets

(56) References Cited

U.S. PATENT DOCUMENTS

| | | |
|---|---|---|
| 3,503,396 A | 3/1970 | Pierie et al. |
| 3,654,965 A | 4/1972 | Gramain |
| 4,041,931 A | 8/1977 | Elliott et al. |
| 4,048,987 A | 9/1977 | Hurson |
| 4,112,932 A | 9/1978 | Chiulli |
| 4,120,302 A | 10/1978 | Ziegler |
| 4,203,430 A | 5/1980 | Takahashi |
| 4,306,545 A | 12/1981 | Ivan et al. |
| 4,373,532 A | 2/1983 | Hill et al. |
| 2,129,391 A | 9/1983 | Frederick |
| 4,402,683 A | 9/1983 | Kopman |
| 4,417,888 A | 11/1983 | Cosentino et al. |
| 4,559,947 A | 12/1985 | Renger et al. |
| 4,608,977 A | 9/1986 | Brown |
| 4,669,473 A | 6/1987 | Richards et al. |
| 4,821,719 A | 4/1989 | Fogarty |
| 4,831,070 A | 5/1989 | McInally et al. |
| 4,880,015 A | 11/1989 | Nierman |
| 5,020,514 A | 6/1991 | Heckele |
| 5,027,800 A | 7/1991 | Rowland |
| 5,058,603 A | 10/1991 | Doi et al. |
| 5,141,498 A | 8/1992 | Christian |
| 5,183,471 A | 2/1993 | Wilk |
| 5,197,955 A | 3/1993 | Stephens et al. |
| 5,201,742 A | 4/1993 | Hasson |
| 5,207,213 A | 5/1993 | Auhll et al. |
| 5,209,737 A | 5/1993 | Ritchart et al. |
| 5,209,741 A | 5/1993 | Spaeth |
| 5,209,747 A | 5/1993 | Knoepfler |
| 5,269,772 A | 12/1993 | Wilk |
| 5,275,614 A | 1/1994 | Haber et al. |
| 5,284,128 A | 2/1994 | Hart |
| 5,308,336 A | 5/1994 | Hart et al. |
| 5,312,023 A | 5/1994 | Green et al. |
| 5,329,923 A * | 7/1994 | Lundquist ............... 600/373 |
| 5,330,437 A | 7/1994 | Durman |
| 5,330,502 A | 7/1994 | Hassler et al. |
| 5,342,396 A | 8/1994 | Cook |
| 5,345,927 A | 9/1994 | Bonutti |
| 5,350,391 A | 9/1994 | Iacovelli |
| 5,360,428 A | 11/1994 | Hutchinson, Jr. |
| 5,362,294 A | 11/1994 | Seitzinger |
| 5,366,478 A | 11/1994 | Brinkerhoff et al. |
| 5,368,597 A | 11/1994 | Pagedas |
| 5,374,277 A | 12/1994 | Hassler |
| 5,381,943 A | 1/1995 | Allen et al. |
| 5,383,888 A | 1/1995 | Zvenyatsky et al. |
| 5,385,553 A | 1/1995 | Hart et al. |
| 5,385,560 A | 1/1995 | Wulf |
| 5,391,154 A | 2/1995 | Young |
| 5,398,617 A | 3/1995 | Deandrea |
| 5,403,342 A | 4/1995 | Tovey et al. |
| 5,417,203 A | 5/1995 | Tovey et al. |
| 5,419,339 A | 5/1995 | Palmer |
| 5,441,483 A * | 8/1995 | Avitall ............... 604/95.05 |
| 5,443,452 A | 8/1995 | Hart et al. |
| 5,443,484 A | 8/1995 | Kirsch et al. |
| 5,445,648 A | 8/1995 | Cook |
| 5,456,684 A | 10/1995 | Schmidt et al. |
| 5,480,410 A | 1/1996 | Cuschieri et al. |
| 5,489,256 A | 2/1996 | Adair |
| 5,489,290 A | 2/1996 | Furnish |
| 5,501,653 A | 3/1996 | Chin |
| 5,514,157 A | 5/1996 | Nicholas et al. |
| 5,520,609 A | 5/1996 | Moll et al. |
| 5,520,678 A * | 5/1996 | Heckele et al. ............... 606/1 |
| 5,545,123 A | 8/1996 | Ortiz et al. |
| 5,545,179 A | 8/1996 | Williamson, IV |
| 5,547,458 A | 8/1996 | Ortiz et al. |
| 5,549,637 A | 8/1996 | Crainich |
| 5,569,205 A | 10/1996 | Hart et al. |
| 5,569,254 A | 10/1996 | Carlson et al. |
| 5,571,090 A | 11/1996 | Sherts |
| 5,571,129 A | 11/1996 | Porter |
| 5,573,520 A * | 11/1996 | Schwartz et al. ............ 604/526 |
| 5,578,048 A | 11/1996 | Pasqualucci et al. |
| 5,582,577 A | 12/1996 | Lund et al. |
| 5,582,617 A | 12/1996 | Klieman et al. |
| 5,584,850 A | 12/1996 | Hart et al. |
| 5,586,977 A | 12/1996 | Dorsey, III |
| 5,591,182 A | 1/1997 | Johnson |
| 5,595,193 A | 1/1997 | Walus et al. |
| 5,607,450 A | 3/1997 | Zvenyatsky et al. |
| 5,609,601 A | 3/1997 | Kolesa et al. |
| 5,618,291 A | 4/1997 | Thompson et al. |
| 5,618,294 A | 4/1997 | Aust et al. |
| 5,624,381 A | 4/1997 | Kieturakis |
| 5,626,608 A | 5/1997 | Cuny et al. |
| 5,630,831 A | 5/1997 | Lahr |
| 5,632,432 A | 5/1997 | Schulze et al. |
| 5,632,734 A | 5/1997 | Galel et al. |
| 5,634,882 A | 6/1997 | Gagner |
| 5,634,883 A | 6/1997 | Chin et al. |
| 5,634,911 A | 6/1997 | Hermann et al. |
| 5,634,937 A | 6/1997 | Mollenauer et al. |
| 5,636,645 A | 6/1997 | Ou |
| 5,640,977 A | 6/1997 | Leahy et al. |
| 5,643,283 A | 7/1997 | Younker |
| 5,643,301 A | 7/1997 | Mollenauer |
| 5,647,372 A | 7/1997 | Tovey et al. |
| 5,653,705 A | 8/1997 | de la Torre et al. |
| 5,665,093 A | 9/1997 | Atkins et al. |
| 5,667,527 A | 9/1997 | Cook |
| 5,672,168 A | 9/1997 | de la Torre et al. |
| 5,676,146 A | 10/1997 | Scarborough |
| 5,676,657 A | 10/1997 | Yoon |
| 5,681,324 A | 10/1997 | Kammerer et al. |
| 5,695,448 A | 12/1997 | Kimura et al. |
| 5,700,275 A | 12/1997 | Bell et al. |
| 5,704,534 A | 1/1998 | Huitema et al. |
| 5,713,919 A | 2/1998 | Lahr |
| 5,716,327 A | 2/1998 | Warner et al. |
| 5,716,407 A | 2/1998 | Knapp et al. |
| 5,728,121 A | 3/1998 | Bimbo et al. |
| 5,735,289 A | 4/1998 | Pfeffer et al. |
| 5,743,456 A | 4/1998 | Jones et al. |
| 5,743,851 A | 4/1998 | Moll et al. |
| 5,766,205 A | 6/1998 | Zvenyatsky et al. |
| 5,772,654 A | 6/1998 | Leyva |
| 5,782,812 A | 7/1998 | Hart et al. |
| 5,782,859 A | 7/1998 | Nicholas et al. |
| 5,792,165 A | 8/1998 | Klieman et al. |
| 5,797,959 A | 8/1998 | Castro et al. |
| 5,803,919 A | 9/1998 | Hart et al. |
| 5,813,409 A | 9/1998 | Leahy et al. |
| 5,814,058 A | 9/1998 | Carlson et al. |
| 5,816,257 A | 10/1998 | Chin |
| 5,827,319 A | 10/1998 | Carlson et al. |
| 5,827,323 A | 10/1998 | Klieman et al. |
| 5,833,692 A | 11/1998 | Cesarini et al. |
| 5,836,960 A | 11/1998 | Kolesa et al. |
| 5,840,078 A | 11/1998 | Yerys |
| 5,853,395 A | 12/1998 | Crook et al. |
| 5,865,807 A | 2/1999 | Blake, III |
| 5,872,859 A | 2/1999 | Gur et al. |
| 5,876,447 A | 3/1999 | Arnett |
| 5,891,013 A | 4/1999 | Thompson |
| 5,893,878 A | 4/1999 | Pierce |
| 5,906,577 A | 5/1999 | Beane et al. |
| 5,921,956 A | 7/1999 | Grinberg et al. |
| 5,941,890 A | 8/1999 | Voegele et al. |
| 5,947,922 A | 9/1999 | MacLeod |
| 5,957,913 A | 9/1999 | de la Torre et al. |
| 5,971,995 A | 10/1999 | Rousseau |
| 5,977,431 A | 11/1999 | Knapp et al. |
| 5,990,382 A | 11/1999 | Fox |
| 6,007,561 A | 12/1999 | Bourque et al. |
| 6,024,708 A | 2/2000 | Bales et al. |
| 6,024,736 A | 2/2000 | de la Torre et al. |
| 6,027,522 A | 2/2000 | Palmer |
| 6,033,428 A | 3/2000 | Sardella |
| RE36,702 E | 5/2000 | Green et al. |
| 6,074,419 A | 6/2000 | Healy et al. |
| 6,077,287 A | 6/2000 | Taylor et al. |

(56) References Cited

U.S. PATENT DOCUMENTS

| | | | |
|---|---|---|---|
| 6,077,288 A | 6/2000 | Shimomura et al. | |
| 6,086,603 A | 7/2000 | Termin et al. | |
| 6,093,141 A | 7/2000 | Mosseri et al. | |
| 6,110,154 A | 8/2000 | Shimomura et al. | |
| 6,110,182 A | 8/2000 | Mowlai-Ashtiani | |
| 6,120,513 A | 9/2000 | Bailey et al. | |
| 6,123,689 A | 9/2000 | To et al. | |
| 6,126,671 A | 10/2000 | Richards et al. | |
| 6,132,385 A | 10/2000 | Vain | |
| 6,149,642 A | 11/2000 | Gerhart et al. | |
| 6,156,045 A | 12/2000 | Ulbrich et al. | |
| 6,156,184 A | 12/2000 | Antonucci et al. | |
| 6,159,200 A | 12/2000 | Verdura et al. | |
| 6,162,196 A | 12/2000 | Hart et al. | |
| 6,162,208 A | 12/2000 | Hipps | |
| 6,165,184 A | 12/2000 | Verdura et al. | |
| 6,171,282 B1 | 1/2001 | Ragsdale | |
| 6,197,034 B1 | 3/2001 | Gvozdic et al. | |
| 6,217,555 B1 | 4/2001 | Hart et al. | |
| 6,220,248 B1 | 4/2001 | Voegele et al. | |
| 6,228,055 B1 | 5/2001 | Foerster et al. | |
| 6,245,011 B1 | 6/2001 | Dudda et al. | |
| 6,245,052 B1 | 6/2001 | Orth et al. | |
| 6,248,062 B1 | 6/2001 | Adler et al. | |
| 6,258,069 B1 | 7/2001 | Carpentier et al. | |
| 6,258,102 B1 | 7/2001 | Pagedas | |
| 6,261,302 B1 | 7/2001 | Voegele et al. | |
| 6,264,599 B1 | 7/2001 | Slater et al. | |
| 6,290,705 B1 | 9/2001 | Chan et al. | |
| 6,293,966 B1 | 9/2001 | Frantzen | |
| 6,315,770 B1 | 11/2001 | de la Torre et al. | |
| 6,319,246 B1 | 11/2001 | de la Torre et al. | |
| 6,347,940 B1 | 2/2002 | Gordils Wallis et al. | |
| 6,348,034 B1 | 2/2002 | Thompson | |
| 6,352,503 B1 | 3/2002 | Matsui et al. | |
| 6,400,979 B1 | 6/2002 | Stoianovici et al. | |
| 6,402,687 B1 * | 6/2002 | Ouchi | 600/139 |
| 6,425,903 B1 | 7/2002 | Voegele | |
| 6,443,960 B1 | 9/2002 | Brabrand et al. | |
| 6,447,443 B1 | 9/2002 | Keogh et al. | |
| 6,447,489 B1 | 9/2002 | Peterson | |
| 6,454,783 B1 | 9/2002 | Piskun | |
| 6,456,184 B1 | 9/2002 | Vu et al. | |
| 6,458,077 B1 | 10/2002 | Boebel et al. | |
| 6,471,714 B1 | 10/2002 | Kim | |
| 6,485,467 B1 | 11/2002 | Crook et al. | |
| 6,494,211 B1 * | 12/2002 | Boyd et al. | 128/898 |
| 6,551,270 B1 | 4/2003 | Bimbo et al. | |
| 6,551,282 B1 | 4/2003 | Exline et al. | |
| 6,578,577 B2 | 6/2003 | Bonadio et al. | |
| 6,579,304 B1 | 6/2003 | Hart et al. | |
| 6,589,167 B1 | 7/2003 | Shimomura et al. | |
| 6,605,063 B2 | 8/2003 | Bousquet | |
| 6,613,068 B2 | 9/2003 | Ouchi | |
| 6,623,426 B2 | 9/2003 | Bonadio et al. | |
| 6,634,883 B2 | 10/2003 | Ranalli | |
| RE38,335 E | 11/2003 | Aust et al. | |
| 6,663,641 B1 | 12/2003 | Kovac et al. | |
| 6,665,554 B1 | 12/2003 | Charles et al. | |
| 6,666,854 B1 | 12/2003 | Lange | |
| 6,669,674 B1 | 12/2003 | Macoviak et al. | |
| 6,673,092 B1 | 1/2004 | Bacher | |
| 6,689,122 B2 | 2/2004 | Yamamoto | |
| 6,706,033 B2 | 3/2004 | Martinez et al. | |
| 6,706,050 B1 | 3/2004 | Giannadakis | |
| 6,725,083 B1 | 4/2004 | Burbank et al. | |
| 6,764,473 B2 | 7/2004 | Morton | |
| 6,766,186 B1 | 7/2004 | Hoyns et al. | |
| 6,807,965 B1 | 10/2004 | Hickle | |
| 6,810,880 B1 | 11/2004 | Jennings, Jr. et al. | |
| 6,818,007 B1 | 11/2004 | Dampney et al. | |
| 6,821,247 B2 | 11/2004 | Vierra et al. | |
| 6,846,287 B2 | 1/2005 | Bonadio et al. | |
| 6,872,433 B2 | 3/2005 | Seward et al. | |
| 6,908,430 B2 | 6/2005 | Caldwell et al. | |
| 6,913,613 B2 * | 7/2005 | Schwarz et al. | 606/206 |
| 6,936,061 B2 | 8/2005 | Sasaki | |
| 6,939,296 B2 | 9/2005 | Ewers et al. | |
| 6,945,932 B1 | 9/2005 | Caldwell et al. | |
| 6,966,876 B2 | 11/2005 | Irion et al. | |
| 6,972,026 B1 | 12/2005 | Caldwell et al. | |
| 6,994,712 B1 | 2/2006 | Fisher et al. | |
| 7,008,377 B2 | 3/2006 | Beane et al. | |
| 7,014,628 B2 | 3/2006 | Bousquet | |
| 7,021,173 B2 | 4/2006 | Stoianovici et al. | |
| 7,047,063 B2 | 5/2006 | Burbank et al. | |
| 7,052,454 B2 | 5/2006 | Taylor | |
| 7,083,576 B2 | 8/2006 | Zarins et al. | |
| 7,083,626 B2 | 8/2006 | Hart et al. | |
| 7,087,071 B2 | 8/2006 | Nicholas et al. | |
| 7,118,528 B1 | 10/2006 | Piskun | |
| 7,147,650 B2 | 12/2006 | Lee | |
| 7,163,510 B2 | 1/2007 | Kahle et al. | |
| 7,201,734 B2 | 4/2007 | Hickle | |
| 7,208,005 B2 | 4/2007 | Frecker et al. | |
| 7,214,185 B1 | 5/2007 | Rosney et al. | |
| 7,247,154 B2 | 7/2007 | Hickle | |
| 7,311,661 B2 | 12/2007 | Heinrich | |
| 7,331,661 B2 | 2/2008 | Silverbrook et al. | |
| 7,331,750 B2 * | 2/2008 | Merz et al. | 414/735 |
| 7,338,473 B2 | 3/2008 | Campbell et al. | |
| 7,344,547 B2 | 3/2008 | Piskun | |
| 7,347,862 B2 | 3/2008 | Layer | |
| 7,416,533 B2 | 8/2008 | Gellman et al. | |
| 7,615,005 B2 | 11/2009 | Stefanchik et al. | |
| 7,691,095 B2 | 4/2010 | Bednarek et al. | |
| 7,909,220 B2 | 3/2011 | Viola | |
| 7,985,239 B2 | 7/2011 | Suzuki | |
| 7,988,699 B2 * | 8/2011 | Martz et al. | 606/99 |
| 8,083,667 B2 * | 12/2011 | Cooper et al. | 600/104 |
| 8,182,418 B2 * | 5/2012 | Durant | A61B 1/0055 600/141 |
| 8,562,592 B2 * | 10/2013 | Conlon | A61B 17/29 600/141 |
| 8,758,232 B2 * | 6/2014 | Graham | A61B 5/065 600/142 |
| 8,821,388 B2 * | 9/2014 | Naito | A61B 1/0055 600/141 |
| 2001/0034528 A1 | 10/2001 | Foerster et al. | |
| 2001/0053510 A1 | 12/2001 | Ranalli | |
| 2002/0007112 A1 | 1/2002 | Rupp et al. | |
| 2002/0026201 A1 | 2/2002 | Foerster et al. | |
| 2002/0103434 A1 | 8/2002 | Swanbom | |
| 2002/0156432 A1 | 10/2002 | Racenet et al. | |
| 2002/0156497 A1 | 10/2002 | Nagase et al. | |
| 2002/0173805 A1 | 11/2002 | Matsuno et al. | |
| 2002/0193815 A1 | 12/2002 | Foerster et al. | |
| 2003/0028179 A1 | 2/2003 | Piskun | |
| 2003/0028207 A1 | 2/2003 | Lang et al. | |
| 2003/0073882 A1 | 4/2003 | Smid et al. | |
| 2003/0100814 A1 | 5/2003 | Kindlein | |
| 2003/0109898 A1 | 6/2003 | Schwarz et al. | |
| 2003/0113540 A1 | 6/2003 | Anderson et al. | |
| 2003/0114838 A1 * | 6/2003 | O'Neill et al. | 606/1 |
| 2003/0120285 A1 | 6/2003 | Kortenbach | |
| 2003/0135204 A1 | 7/2003 | Lee et al. | |
| 2003/0139756 A1 | 7/2003 | Brustad | |
| 2003/0206860 A1 | 11/2003 | Bleyer et al. | |
| 2003/0208207 A1 | 11/2003 | Layer | |
| 2003/0225420 A1 | 12/2003 | Wardle | |
| 2003/0229338 A1 | 12/2003 | Irion et al. | |
| 2003/0236549 A1 | 12/2003 | Bonadio et al. | |
| 2004/0015185 A1 | 1/2004 | Ewers et al. | |
| 2004/0023161 A1 | 2/2004 | Yamaguchi et al. | |
| 2004/0024304 A1 | 2/2004 | Foerster et al. | |
| 2004/0068291 A1 | 4/2004 | Suzuki | |
| 2004/0106942 A1 | 6/2004 | Taylor et al. | |
| 2004/0106986 A1 | 6/2004 | Andersson et al. | |
| 2004/0138525 A1 | 7/2004 | Saadat et al. | |
| 2004/0138528 A1 | 7/2004 | Richter et al. | |
| 2004/0147933 A1 | 7/2004 | McGovern | |
| 2004/0167545 A1 | 8/2004 | Sadler et al. | |
| 2004/0193146 A1 | 9/2004 | Lee et al. | |
| 2004/0193212 A1 | 9/2004 | Taniguchi et al. | |

(56) References Cited

U.S. PATENT DOCUMENTS

| | | |
|---|---|---|
| 2004/0215063 A1 | 10/2004 | Bonadio et al. |
| 2004/0225323 A1 | 11/2004 | Nagase et al. |
| 2004/0230160 A1 | 11/2004 | Blanco |
| 2004/0230161 A1 | 11/2004 | Zeiner |
| 2004/0243108 A1 | 12/2004 | Suzuki |
| 2004/0254426 A1 | 12/2004 | Wenchell |
| 2004/0260198 A1 | 12/2004 | Rothberg et al. |
| 2004/0260337 A1 | 12/2004 | Freed |
| 2005/0020884 A1 | 1/2005 | Hart et al. |
| 2005/0033312 A1 | 2/2005 | Suzuki |
| 2005/0033342 A1 | 2/2005 | Hart et al. |
| 2005/0033357 A1 | 2/2005 | Braun |
| 2005/0049580 A1 | 3/2005 | Brock et al. |
| 2005/0085842 A1 | 4/2005 | Eversull et al. |
| 2005/0090809 A1* | 4/2005 | Cooper et al. ............... 606/1 |
| 2005/0107809 A1 | 5/2005 | Litscher et al. |
| 2005/0124912 A1 | 6/2005 | Griego et al. |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0192483 A1 | 9/2005 | Bonadio et al. |
| 2005/0209608 A1 | 9/2005 | O'Heeron |
| 2005/0222582 A1 | 10/2005 | Wenchell |
| 2005/0228224 A1 | 10/2005 | Okada et al. |
| 2005/0267419 A1 | 12/2005 | Smith |
| 2005/0273084 A1 | 12/2005 | Hinman et al. |
| 2005/0273132 A1 | 12/2005 | Shluzas et al. |
| 2005/0277946 A1 | 12/2005 | Greenhalgh |
| 2006/0016853 A1 | 1/2006 | Racenet |
| 2006/0020241 A1 | 1/2006 | Piskun et al. |
| 2006/0020281 A1 | 1/2006 | Smith |
| 2006/0020287 A1 | 1/2006 | Lee et al. |
| 2006/0042636 A1 | 3/2006 | Nalagatla et al. |
| 2006/0071432 A1 | 4/2006 | Staudner |
| 2006/0094933 A1 | 5/2006 | Goldfarb et al. |
| 2006/0149137 A1 | 7/2006 | Pingleton et al. |
| 2006/0206145 A1 | 9/2006 | Griego et al. |
| 2006/0212062 A1 | 9/2006 | Farascioni |
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0229641 A1 | 10/2006 | Gupta et al. |
| 2006/0229665 A1 | 10/2006 | Wales et al. |
| 2006/0241651 A1 | 10/2006 | Wilk |
| 2006/0241671 A1 | 10/2006 | Greenhalgh |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0258899 A1 | 11/2006 | Gill et al. |
| 2006/0259071 A1 | 11/2006 | Nicholas et al. |
| 2006/0259073 A1 | 11/2006 | Miyamoto et al. |
| 2006/0264706 A1 | 11/2006 | Piskun |
| 2006/0270911 A1 | 11/2006 | Voegele et al. |
| 2007/0027468 A1 | 2/2007 | Wales et al. |
| 2007/0049966 A1 | 3/2007 | Bonadio et al. |
| 2007/0060939 A1 | 3/2007 | Lancial et al. |
| 2007/0085232 A1 | 4/2007 | Brustad et al. |
| 2007/0088202 A1 | 4/2007 | Albrecht et al. |
| 2007/0088277 A1 | 4/2007 | McGinley et al. |
| 2007/0106317 A1 | 5/2007 | Shelton et al. |
| 2007/0118021 A1 | 5/2007 | Pokorney |
| 2007/0151566 A1 | 7/2007 | Kahle et al. |
| 2007/0156119 A1 | 7/2007 | Wallace et al. |
| 2007/0162072 A1 | 7/2007 | Nicholas et al. |
| 2007/0179525 A1 | 8/2007 | Frecker et al. |
| 2007/0185453 A1 | 8/2007 | Michael et al. |
| 2007/0208312 A1 | 9/2007 | Norton et al. |
| 2007/0244358 A1 | 10/2007 | Lee |
| 2007/0250113 A1 | 10/2007 | Hegeman et al. |
| 2007/0255219 A1 | 11/2007 | Vaugh et al. |
| 2007/0260114 A1* | 11/2007 | Miyamoto et al. ......... 600/114 |
| 2008/0027476 A1 | 1/2008 | Piskun |
| 2008/0039892 A1* | 2/2008 | Mitsuishi et al. ............ 606/208 |
| 2008/0045803 A1 | 2/2008 | Williams et al. |
| 2008/0051631 A1* | 2/2008 | Dejima ............... A61B 1/0052 600/114 |
| 2008/0051739 A1 | 2/2008 | McFarlane |
| 2008/0064921 A1* | 3/2008 | Larkin et al. ................. 600/104 |
| 2008/0065021 A1 | 3/2008 | Jenkins et al. |
| 2008/0065107 A1 | 3/2008 | Larkin et al. |
| 2008/0105730 A1 | 5/2008 | Racenet et al. |
| 2008/0119821 A1 | 5/2008 | Agnihotri et al. |
| 2008/0147113 A1 | 6/2008 | Nobis et al. |
| 2008/0154299 A1 | 6/2008 | Livneh |
| 2008/0177134 A1 | 7/2008 | Miyamoto et al. |
| 2008/0183044 A1 | 7/2008 | Colleran et al. |
| 2008/0188891 A1 | 8/2008 | Frank et al. |
| 2008/0255420 A1 | 10/2008 | Lee et al. |
| 2008/0255519 A1 | 10/2008 | Piskun et al. |
| 2008/0255608 A1 | 10/2008 | Hinman et al. |
| 2008/0262492 A1 | 10/2008 | Lee |
| 2008/0269727 A1 | 10/2008 | Lee |
| 2008/0294154 A1* | 11/2008 | Ibrahim et al. ................. 606/13 |
| 2008/0294191 A1 | 11/2008 | Lee |
| 2009/0005799 A1 | 1/2009 | Franer et al. |
| 2009/0062618 A1 | 3/2009 | Drew et al. |
| 2009/0084826 A1 | 4/2009 | Shah et al. |
| 2009/0088792 A1 | 4/2009 | Hoell, Jr. et al. |
| 2009/0112230 A1 | 4/2009 | Jinno |
| 2009/0171147 A1 | 7/2009 | Lee et al. |
| 2009/0206129 A1 | 8/2009 | Doll et al. |
| 2009/0306658 A1 | 12/2009 | Nobis et al. |
| 2009/0326325 A1* | 12/2009 | Naito ................... A61B 1/0055 600/141 |
| 2010/0057121 A1* | 3/2010 | Piskun et al. ................. 606/206 |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094289 A1* | 4/2010 | Taylor et al. .................... 606/52 |
| 2010/0130817 A1* | 5/2010 | Conlon ......................... 600/106 |
| 2010/0179540 A1* | 7/2010 | Marczyk et al. ................ 606/41 |
| 2010/0228090 A1 | 9/2010 | Weisenburgh, II et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0228096 A1 | 9/2010 | Weisenburgh, II et al. |
| 2010/0228198 A1 | 9/2010 | Widenhouse et al. |
| 2010/0261975 A1 | 10/2010 | Huey et al. |
| 2010/0312060 A1 | 12/2010 | Widenhouse et al. |
| 2010/0312061 A1 | 12/2010 | Hess et al. |
| 2010/0312064 A1 | 12/2010 | Weisenburgh, II et al. |
| 2010/0312065 A1 | 12/2010 | Shelton, IV et al. |
| 2010/0331857 A1* | 12/2010 | Doyle et al. ................... 606/130 |
| 2011/0027269 A1 | 2/2011 | Marrotta et al. |
| 2011/0028793 A1 | 2/2011 | Martin et al. |
| 2011/0028794 A1 | 2/2011 | Widenhouse et al. |
| 2011/0087236 A1* | 4/2011 | Stokes et al. .................. 606/130 |
| 2011/0230875 A1* | 9/2011 | Walberg et al. ................. 606/33 |
| 2011/0275901 A1 | 11/2011 | Shelton, IV |
| 2011/0276057 A1 | 11/2011 | Conlon et al. |
| 2011/0276083 A1 | 11/2011 | Shelton, IV et al. |
| 2011/0276084 A1 | 11/2011 | Shelton, IV |
| 2012/0024099 A1* | 2/2012 | Main ............................... 74/470 |
| 2012/0078243 A1 | 3/2012 | Worrell et al. |
| 2014/0039518 A1 | 2/2014 | Conlon et al. |
| 2015/0119918 A1* | 4/2015 | Blase et al. .................... 606/170 |

FOREIGN PATENT DOCUMENTS

| | | |
|---|---|---|
| DE | 9419138 U1 | 3/1995 |
| DE | 19520717 A1 | 12/1996 |
| DE | 202007003093 U1 | 7/2007 |
| EP | 0568383 A1 | 11/1993 |
| EP | 0621009 A1 | 10/1994 |
| EP | 0646358 A1 | 4/1995 |
| EP | 0776231 A1 | 6/1997 |
| EP | 0950376 A1 | 10/1999 |

(56) References Cited

FOREIGN PATENT DOCUMENTS

| | | |
|---|---|---|
| EP | 0966924 A1 | 12/1999 |
| EP | 0996925 A1 | 5/2000 |
| EP | 1219251 A1 | 7/2002 |
| EP | 1219252 A1 | 7/2002 |
| EP | 1219253 A1 | 7/2002 |
| EP | 1350476 A1 | 10/2003 |
| EP | 1621139 A2 | 2/2006 |
| EP | 1731105 A1 | 12/2006 |
| FR | 2710270 A1 | 3/1995 |
| JP | 2000033089 A | 2/2000 |
| JP | 2006320750 A | 11/2006 |
| WO | WO-9426175 A1 | 11/1994 |
| WO | WO-9608208 A1 | 3/1996 |
| WO | WO-9608897 A1 | 3/1996 |
| WO | WO-9712557 A1 | 4/1997 |
| WO | WO-9729709 A1 | 8/1997 |
| WO | WO-9735521 A1 | 10/1997 |
| WO | WO-9810712 A1 | 3/1998 |
| WO | WO-9903536 A1 | 1/1999 |
| WO | WO-0030592 A1 | 6/2000 |
| WO | WO-0032253 A1 | 6/2000 |
| WO | WO-0217810 A2 | 3/2002 |
| WO | WO-0239890 A2 | 5/2002 |
| WO | WO-0239918 A1 | 5/2002 |
| WO | WO-02058543 A2 | 8/2002 |
| WO | WO-02094133 A1 | 11/2002 |
| WO | WO-03005890 A2 | 1/2003 |
| WO | WO-03067341 A2 | 8/2003 |
| WO | WO-03077730 A2 | 9/2003 |
| WO | WO-03091839 A2 | 11/2003 |
| WO | WO-2005/087112 A1 | 9/2005 |
| WO | WO-2005/094432 A2 | 10/2005 |
| WO | WO-2006/110733 A2 | 10/2006 |
| WO | WO-2007/119232 A2 | 10/2007 |
| WO | WO-2008/012787 A2 | 1/2008 |
| WO | WO-2008/024502 A2 | 2/2008 |
| WO | WO-2009/073577 A2 | 6/2009 |
| WO | WO-2010/030114 A2 | 3/2010 |

OTHER PUBLICATIONS

"Applied GelPort System" by Applied Medical Resources Corporation (2004).
"Bard® Bi-Directional and Kelly-Wick Tunnelers—Instructions for Use," by Bard Peripheral Vascular (Apr. 2006).
"intrack XT—Low Profile Atraumatic Clamps," by Novare Surgical Systems, Inc. (2002).
"1 Lap Disc Hand Access Device—Ref. Ld111," by Ethicon Endo-Surgery, Inc. (date unknown but no later than May 15, 2007, date of citation in U.S. Appl. No. 11/398,985; 1 page).
"Adult Cardiac Surgical Instruments," from the website of Genesee BioMedical, Inc. (date of first publication unknown; downloaded May 3, 2007; 4 pages).
"Hand Instruments," from the website of Olympus Surgical America (date of first publication unknown; downloaded May 3, 2007; 4 pages).
"Pen Competitors," (date of first publication unknown but no later than May 15, 2007, date of citation in U.S. Appl. No. 11/398,985; 1 page).
Advanced Surgical Concepts (ASC), 510(k) TriPort Laparoscopic Access Device, Dec. 26, 2007, 8 pages.
Ashida, R. et al., "Indocyanine Green is an Ideal Dye for Endoscopic Ultrasound-Guided Fine-Needle Tattooing of Pancreatic Tumors" *Endoscopy*, 38, pp. 190-192 (2006).
Desai, M. et al., "Laprascopic and Robtoic Urology: Scarless single port transumbilical nephrectomy and pyeloplasty: first clinical report," Journal Compilation, 2008 BJU International, 101, 83-88.
http://www.innomedic.de/en/products/innomotion_overview.php (Innomedic Products), accessed Oct. 24, 2006.
http://www.intuitivesurgical.com/products/index.aspx (Intuitive Surgical Products), accessed Oct. 24, 2006.
http://www.lap-laser.com/e/laser_m/prod/med.html (LAP Laser Application), accessed Oct. 24, 2006.
Ideas for Surgery.com, "Surgeon performs single-port laparoscopic surgery," dated Dec. 1, 2007.
International Search Report for PCT/US2011/035511 dated Oct. 10, 2011.
International Search Report and Written Opinion for Application No. PCT/US2011/035525, issued Aug. 19, 2011. (12 pages).
International Preliminary Report on Patentability for Application No. PCT/US2011/035525, issued Nov. 13, 2012. (7 pages).
International Search Report and Written Opinion for Application No. PCT/US2011/035526, issued Aug. 19, 2011. (12 pages).
International Preliminary Report on Patentability for Application No. PCT/US2011/035526, issued Nov. 13, 2012. (7 pages).
Lee, D.I. et al., "Novel Approach to Minimizing Trocar Sites during Challenging Hand-Assisted Laparoscopic Surgery Utilizing the Gelport: Trans-Gel Instrument Insertion and Utilization," *Journal of Endourology*, vol. 17, No. 2, pp. 69-71 (Mar. 2003).
Maurin, et al., "A new robotic system for CT-guided percutaneous procedures with haptic feedback," LSIIT (UMR CNRS-ULP 7005), Louis Pasteur University, Bd. S. Brant, BP 10413, Strasbourg Illkirch 67412, France.
Maurin, et al., "A Parallel 5 DOF Positioner for Semi-Spherical Workspaces", Proceedings of DETC'04, ASME 2004 Design Engineering Technical Conferences and Computers and Information in Engineering Conference, Sep. 28-Oct. 2, 2004, Salt Lake City Utah USA.
Maurin, et al., "A Parallel Robotic System with Force Sensors for Percutaneous Procedures Under CT-Guidance", LSIIT (UMR CNRS-ULP 7005), Strasbourg I University Bd. S. Brant, BP 10413, 67412 Illkirch cedex, France.
Stoianovici, et al., "A Novel Mechanical Transmission Applied to Percutaneous Renal Access", DSC—vol. 61, Proceedings of the ASME Dynamic Systems and Control Division 1997.
*Twentieth Edition—Illustrations of Surgical Instruments*, by The Kny-Scheerer Company, New York, USA, pp. 1003, 1026, 1028-1029, 1133, 2034, 2068-2069, 2097-2099, 2132, 2137, 2144, 2155-2156, 2162, 2167-2171, 2173, 2175, 2244, 2255, 2281-2282, 2327, 2333, 2338-2348, 2352, 2355, 2359, 2371, 3017, 3039-3073, 3132, 3165, 3168-3169, 3208-3209, 3219 (Jul. 1915).
URobitics, Brady Urological Institute, Johns Hopkins Medical Institutions, "*Z-Stage PAKY*", date of publication unknown but no later than Oct. 26, 2006 (date of citation in U.S. Appl. No. 11/307,231).
URobotics, Brady Urological Institute, Johns Hopkins Medical Institutions, "*PAKY Needle Driver*," date of publication unknown but no later than Oct. 26, 2006 (date of citation in U.S. Appl. No. 11/307,231).
URobotics, Brady Urological Institute, Johns Hopkins Medical Institutions, "*The RCM Robot*", date of publication unknown but no later than Oct. 26, 2006 (date of citation in U.S. Appl. No. 11/307 231).
*Webpage of Novare Surgical, Inc. featuring clamps* (date of first publication unknown; downloaded Feb. 23, 2004; 1 page).
Written Opinion issued in International Application No. PCT/US2011/035526 dated Aug. 19, 2011.

\* cited by examiner

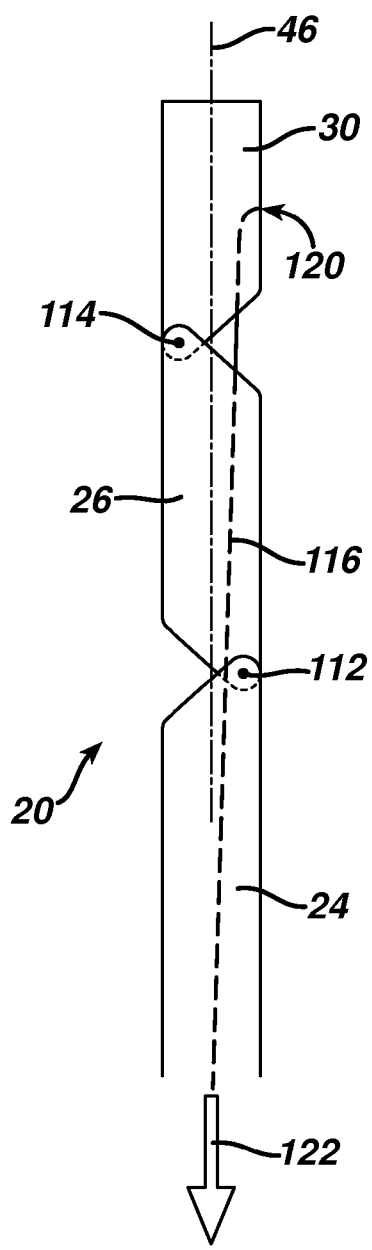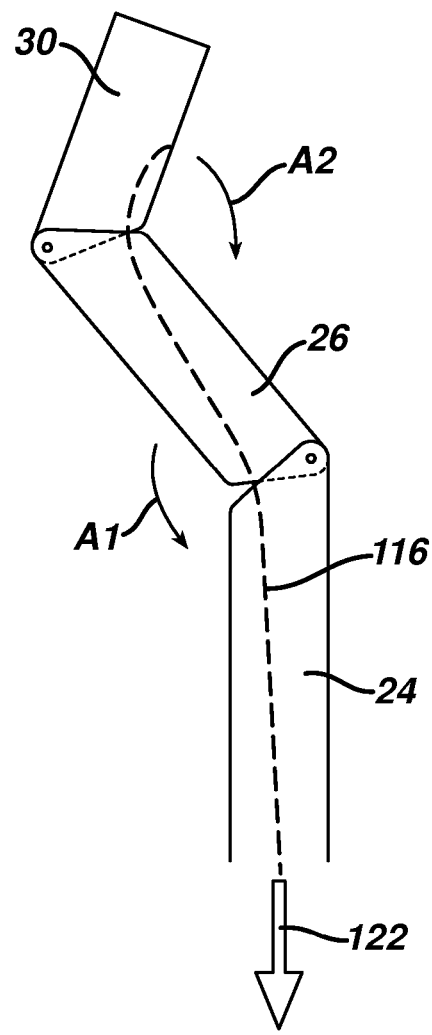
FIG. 13A  FIG. 13B

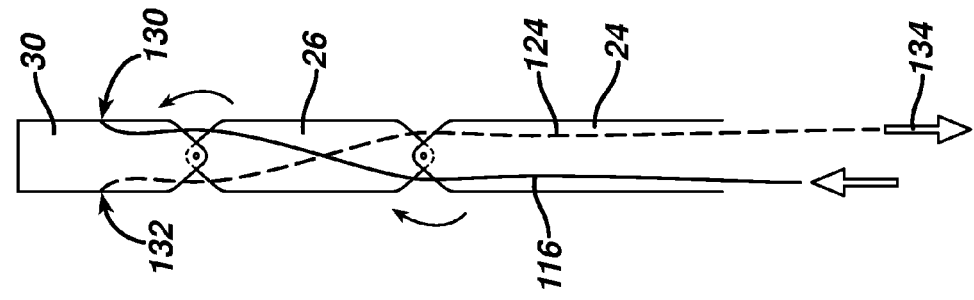
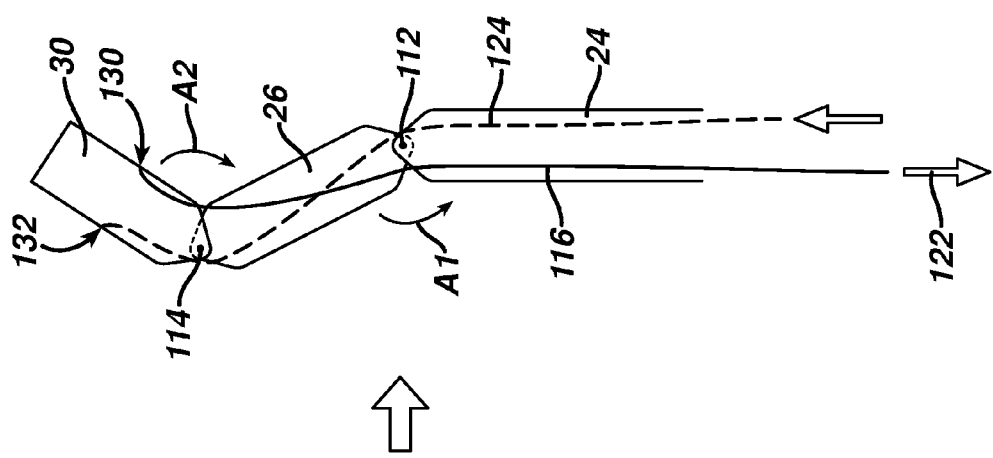
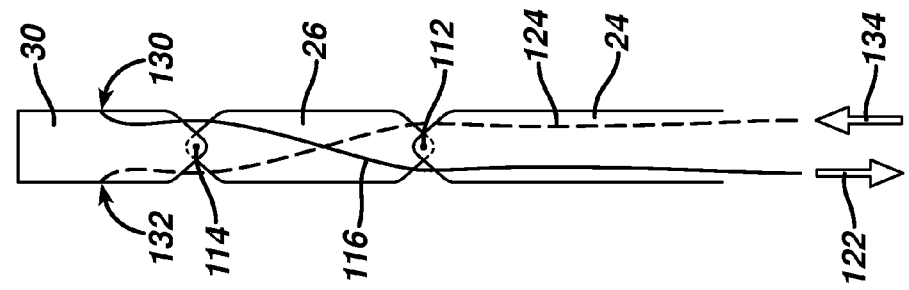

FIG. 17A
FIG. 17B
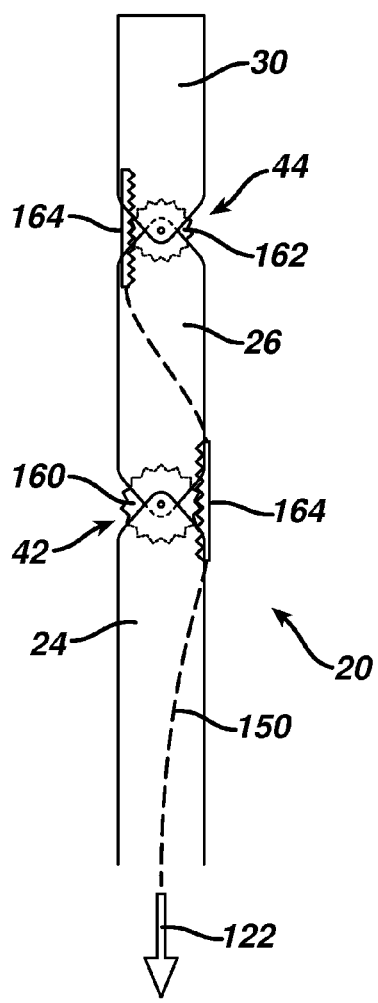
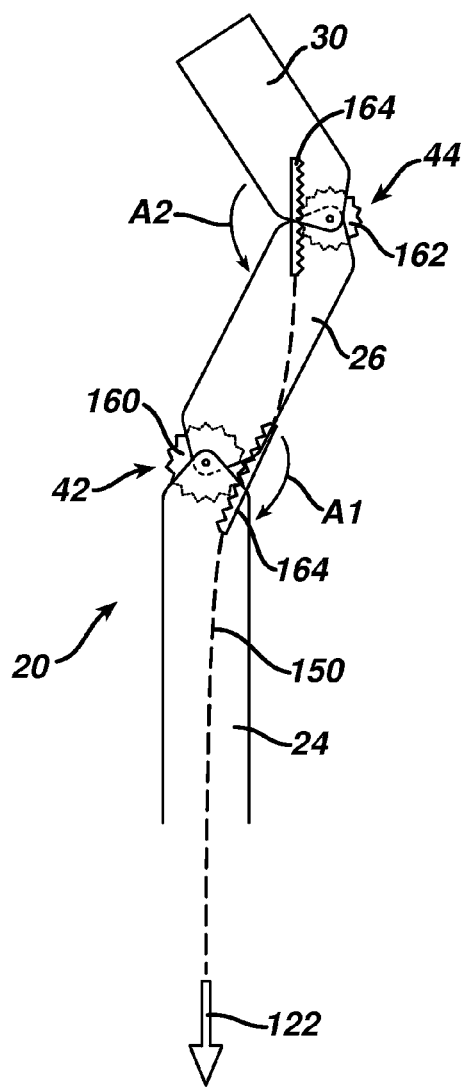

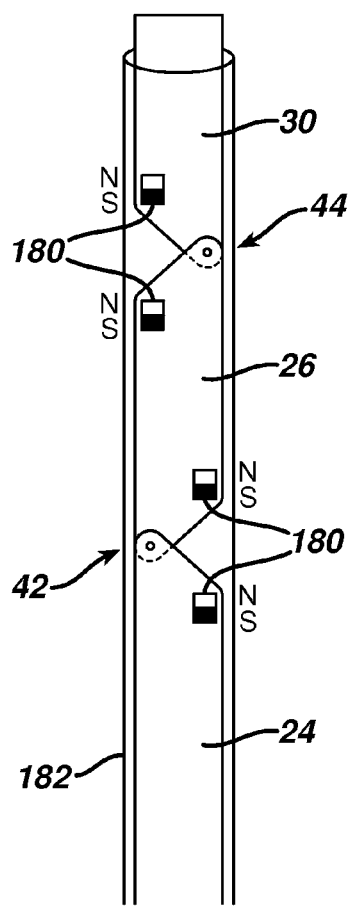
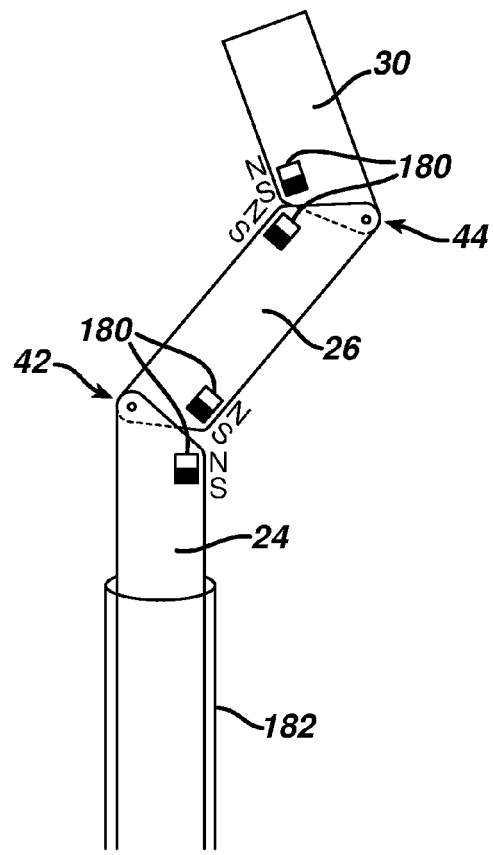
FIG. 19A  FIG. 19B

ARTICULABLE LAPAROSCOPIC INSTRUMENT

RELATED APPLICATIONS

This application claims the benefit of U.S. provisional application No. 61/249,780 filed on 8 Oct. 2009.

FIELD

The present invention relates generally to surgical instruments for minimally invasive surgical procedures and, more particularly, to a laparoscopic surgical instrument having a shaft that can be articulated for positioning a working end at various complex angles to provide improved visualization, manipulation, and access to a surgical site. In particular, the present invention provides a surgical instrument with an articulating shaft for use with a single incision, multiple device access port wherein the shaft can be formed into a triangulated shape to allow multiple instrument tips to come together at a surgical site.

BACKGROUND

Minimally invasive, laparoscopic surgical procedures have become the preferred surgical technique for treating a number of different medical conditions, and the variety of laparoscopic procedures continues to increase. Laparoscopic surgical procedures are often preferred over more traditional open surgical procedures since the smaller incisions tend to reduce the post-operative recovery time and complications. In laparoscopic procedures, surgery is performed in the interior of the abdomen through a number of small incisions. A trocar or cannula is inserted into each of the incisions to provide access to the surgical site.

Laparoscopic procedures generally require the surgeon to act on organs, tissues and/or vessels far removed from the incisions. Thus, the instruments used in such procedures are typically long and narrow, while being functionally controllable from a proximal end of the instrument. Traditionally, many laparoscopic instruments have a generally stiff, straight shaft to facilitate placement through the trocar ports. Such instruments can have working tips rotatable about the shaft axis, while maintaining a linear relationship with the shaft.

The use of straight instrument shafts limits the positioning range of the distal working end of the instrument at the surgery site. The limited ability to manipulate the working end of the instrument has been partially overcome in the past by the use of multiple incisions spaced apart at distances of between 6-9 inches. Spacing apart the multiple incisions has allowed the straight instrument shafts to be directed towards the central surgical site at various angles from the incisions.

Articulation assemblies for use with surgical instruments have also been employed. For instance, U.S. Pat. No. 5,704,534 to Huitema et al, incorporated herein by reference, discloses an articulating surgical instrument and remotely articulating an end effector of an instrument.

Recently, there has been great interest in reducing the number of access incisions for laparoscopic procedures. Limiting the procedures to a single access incision, such as through the navel, or a few closely placed incisions, reduces the risk of infection, as well as the healing time, pain, and scarring of the patient.

Co-pending and commonly assigned patent application Ser. Nos. 12/399,482; 12/399,473; 12/512,542; and 12/512,568 disclose access devices and methods for introducing multiple instruments and/or a laparoscope through a single incision, such as at the navel. Such access devices can include multiple instrument openings spaced relatively closely together.

When using straight shafted instruments with a single or closely spaced access ports, the shafts extend substantially parallel through the ports, which can make it difficult to bring the instrument tips together in a working relationship at the surgical site. Furthermore, it is difficult to have full visualization of the surgical site through the laparoscope due to the spacing between the parallel tips. In order to effectively perform a procedure, the working ends of the various instruments must be able to approach the surgical site from different angles. Thus, to effectively place the working tips of laparoscopic instruments from a single access incision into the desired operative positions requires increased maneuverability of the instrument shafts.

With the foregoing in mind, Applicants have recognized the desirability of having a surgical instrument that provides for precise placement of a working end at a surgical site, including the desirability of having a surgical instrument in which the precise positioning of the working end is obtainable by articulating and rotating the instrument shaft. Further, Applicants have recognized the desirability of having a surgical instrument in which a distal portion of the instrument shaft can be articulated to provide a compound angle relative to a shaft axis to increase the flexibility in positioning the working tip, such as to position the working tip within a field of view of a laparoscope inserted through the same access device through which the instrument shaft is inserted.

Applicants have also recognized the desirability of having an surgical instrument in which the instrument shaft can be inserted in a straight configuration along with other instruments through a single incision, multiple device access port and subsequently articulated to a generally triangular configuration, to precisely position the distal working end in close, non-interfering proximity with other instrument tips at the surgical site. Yet further still, it can be desirable to have such a surgical instrument in which the operation of the working end and articulation of the instrument shaft can be separately and easily controlled using an external handle.

SUMMARY

In one embodiment, a surgical instrument has a handle portion, a working end, such as comprising an end effector for grasping and/or manipulating tissue, and a shaft extending at least part way from the handle to the working end. The shaft can include a proximal shaft segment extending from an instrument handle, and at least two relatively distal shaft segments associated with a distal portion of the instrument shaft. The two (or more) shaft segments can be actuated from a first generally straight configuration in which the two distal shaft segments are generally aligned in a generally straight line with the proximal shaft segment, to a second articulated configuration to form a compound angle, where one of the more distal shaft segments is rotated in an opposite sense from rotation of another of the more distal shaft segments.

The shaft may include a first (or primary) proximal shaft segment; a second central or intermediate shaft segment pivotably connected to a distal portion of the proximal shaft segment; and a third shaft segment pivotably connected to a distal portion of the second shaft segment. A working end, such as an end effector having jaws, can be operatively associated with the distal end of the third shaft segment, such that the end effector jaws can be rotated about a longitudinal axis of the third shaft segment.

In one embodiment, articulation can be provided at least in part by an assembly comprising a multiple linkage apparatus, such as four bar linkage mechanism. For example, at least a portion of the second shaft segment may serve as one of the link members in the four bar linkage mechanism, and at least a portion of the third shaft segment may act as another of the link members.

The instrument may further include first and second link members serving as the other two link members of the four bar mechanism. A proximal end of the first link member may be operatively associated with an actuator in the handle, and the distal portion of the first link member, which can have a "dog leg" shape, may be pivotably connected at a first pivot location to a proximal portion of the second link member. The first link member may also be pivotably connected to a proximal portion of the second shaft segment at a second pivot location spaced apart from the first pivot location. The second link member, in addition to having a proximal portion pivotably connected to first link member, can also have a distal portion pivotably connected to a proximal portion of the third shaft segment.

The instrument shaft may be articulated to have first, second and third shaft segments take on a triangular configuration, and to have a distal end of a second shaft segment rotate away from an axis associated with the first shaft segment, and a distal end of a third shaft segment rotate back toward the axis of the first shaft segment. In such a triangular configuration, the working end of the instrument, such as a grasper, can be conveniently oriented to have a desired position and angular orientation with respect to a surgical site (such as viewed through a laparoscope). Two or more such instruments may be used in a relatively close, non-interfering relationship with each other, or with other instruments. Additionally, the working end can be rotated with respect to the distal most shaft segment while the instrument shaft is in a triangular configuration.

BRIEF DESCRIPTION OF THE DRAWINGS

FIG. 11 further illustrating the proximal portions of the instrument shafts positioned outside the body can have a bend or angle so that the handles of the instruments are less likely to hit or interfere with one another when the instrument shafts are inserted into the instrument openings of the access port;

FIGS. 13A and 13B are schematic diagrams of the distal end of an instrument shaft showing a second embodiment for articulating the shaft;

FIGS. 14A, 14B, and 14C are schematic diagrams of the distal end of an instrument shaft showing a third embodiment for articulating the shaft;

FIGS. 17A and 17B are schematic diagrams of the distal end of the instrument shaft showing a fifth embodiment for articulating the shaft;

FIGS. 19A and 19B are schematic diagrams of the distal end of the instrument shaft, showing a seventh embodiment for articulating the shaft.

DETAILED DESCRIPTION

Figure 1:
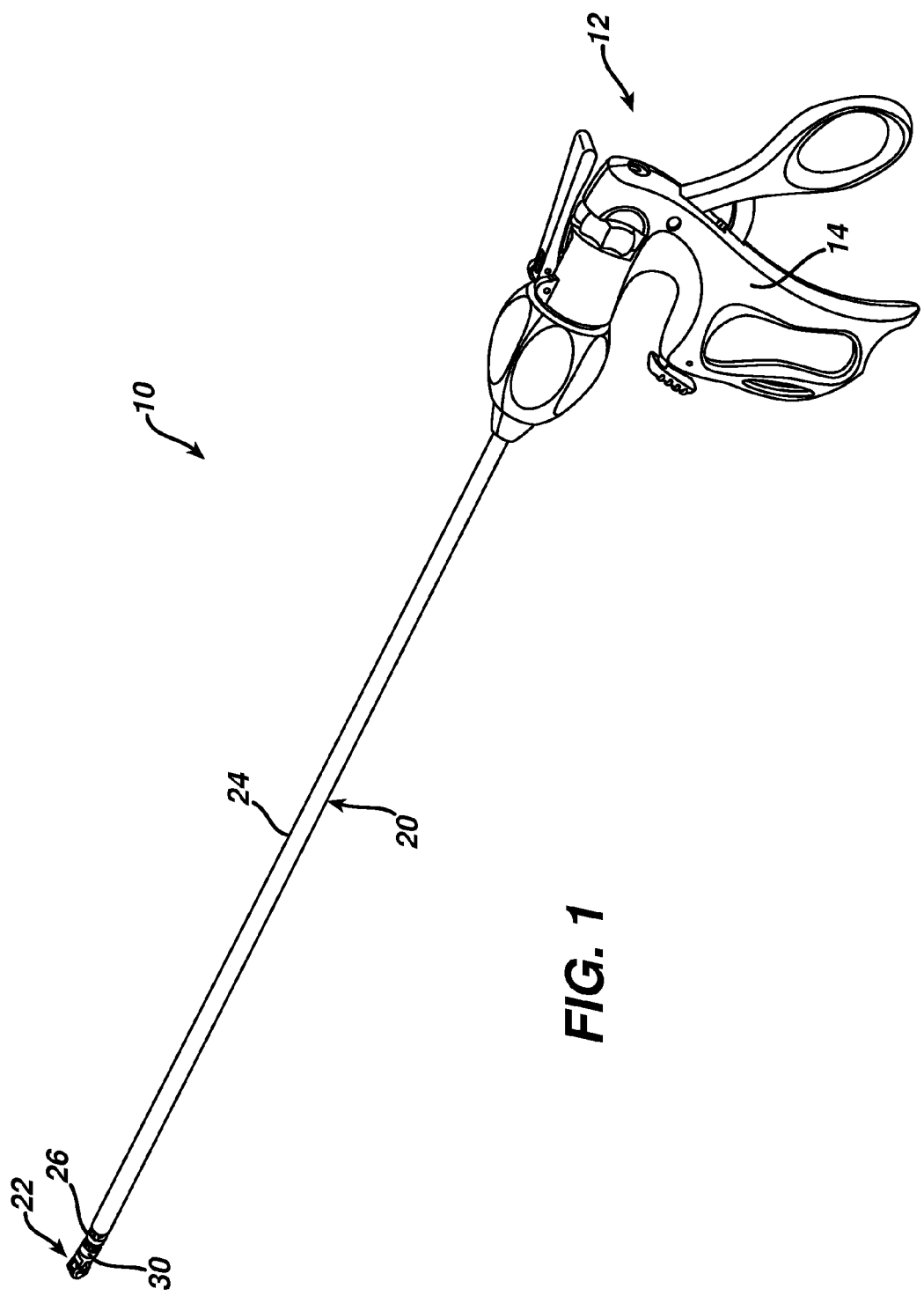
FIG. 1 is a perspective view of an exemplary surgical instrument showing a first embodiment of an articulating shaft.

Turning now to the drawing figures, wherein like numerals indicate like elements throughout the views, FIG. 1-10 illustrate an exemplary surgical instrument. As shown in FIG. 1, instrument 10 can include a proximal handle portion 12 having a pistol grip 14 shaped for gripping by a surgeon. An elongated, tubular shaft 20 extends distally from handle 12.

Figure 11:
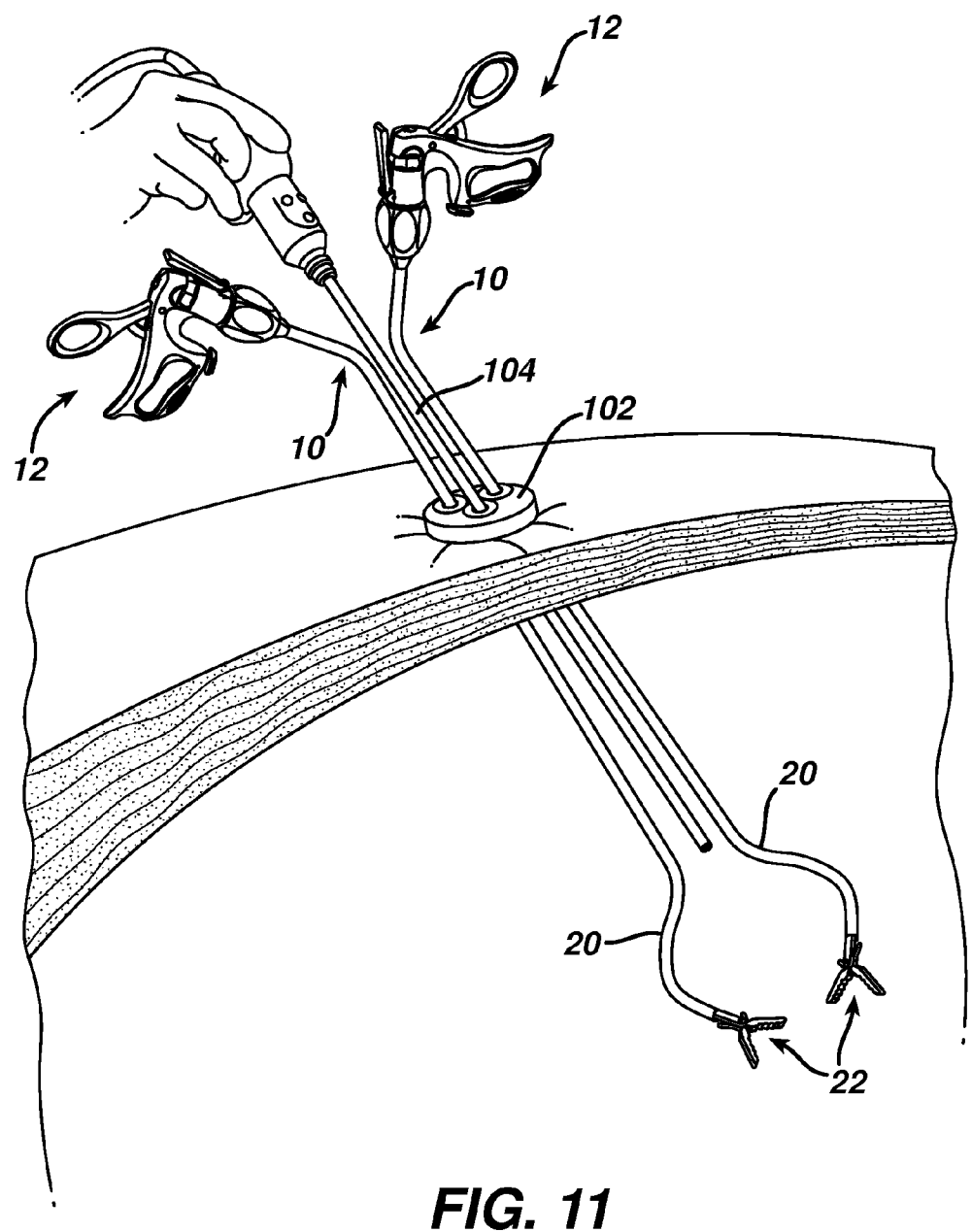
FIG. 11 is a diagrammatic view of a laparoscopic procedure using a single incision, multiple device access port having multiple instrument openings, a laparoscope inserted into the access port, and two instruments having articulating shafts.

Shaft 20 can include multiple shaft segments, and can have a diameter that is less than or equal to about 10 mm, and more particularly less than or equal to about 5 mm to allow for insertion of the shaft through a trocar (not shown) or an instrument opening of a multiple instrument access port of the type illustrated in FIG. 11, such as during a laparoscopic surgical procedure.

A working element 22 is attached to the distal end of shaft 20. Working element 22 can comprise any of a variety of end effectors useable in a surgical procedure and sized for passage through a relatively small (5 mm or less) trocar port including, but not limited to, graspers, dissectors, scissors, and forceps. In the exemplary embodiment shown and described herein, working element 22 is a tissue grasper having a pair of reciprocating jaws for engaging and manipulating a section of tissue. Handle 12 includes controls for operating the distal end effector as well as articulating and rotating the instrument shaft.

Figure 2:
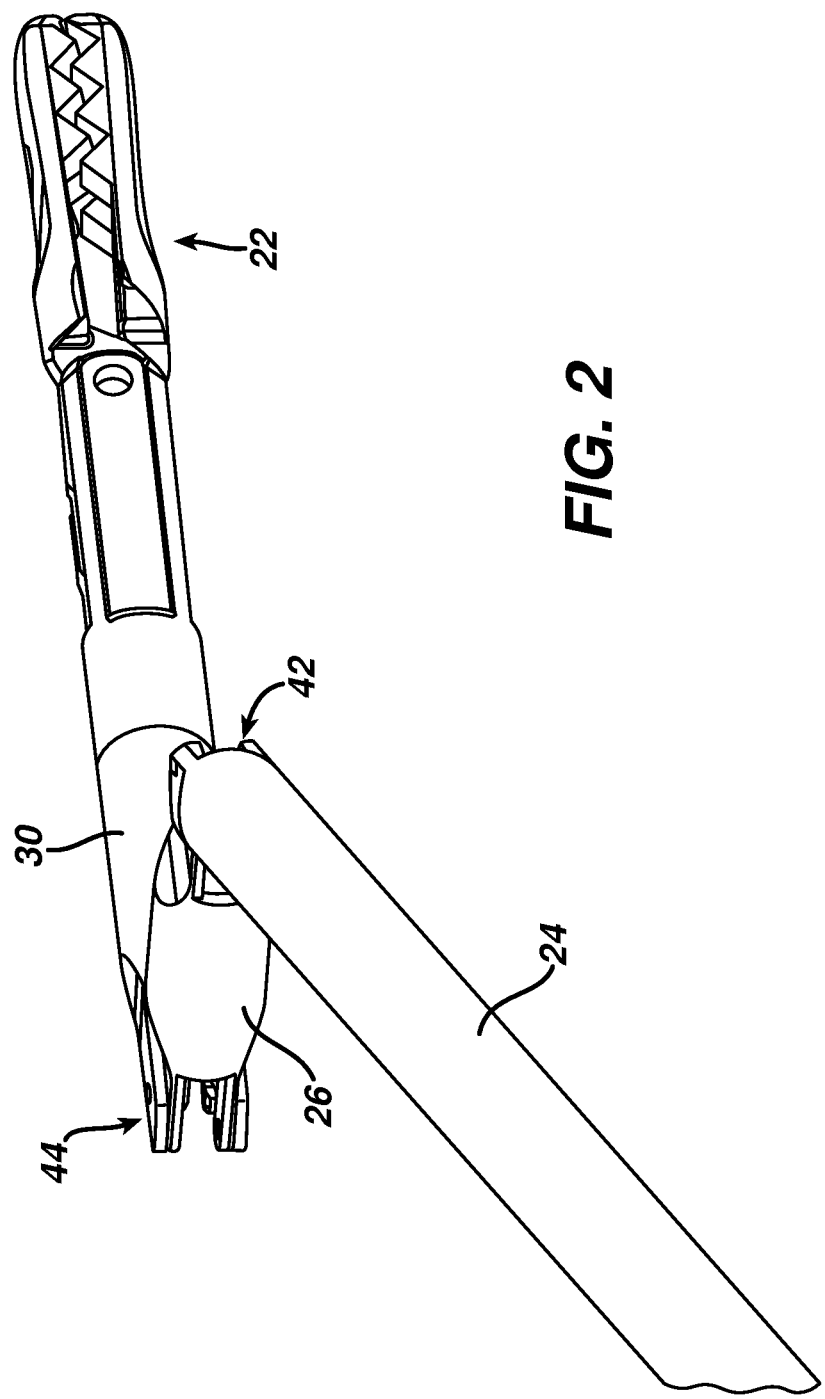
FIG. 2 is a perspective view of the distal end of the instrument shown in FIG. 1, showing the instrument shaft articulated into a compound angle.
Figure 3:
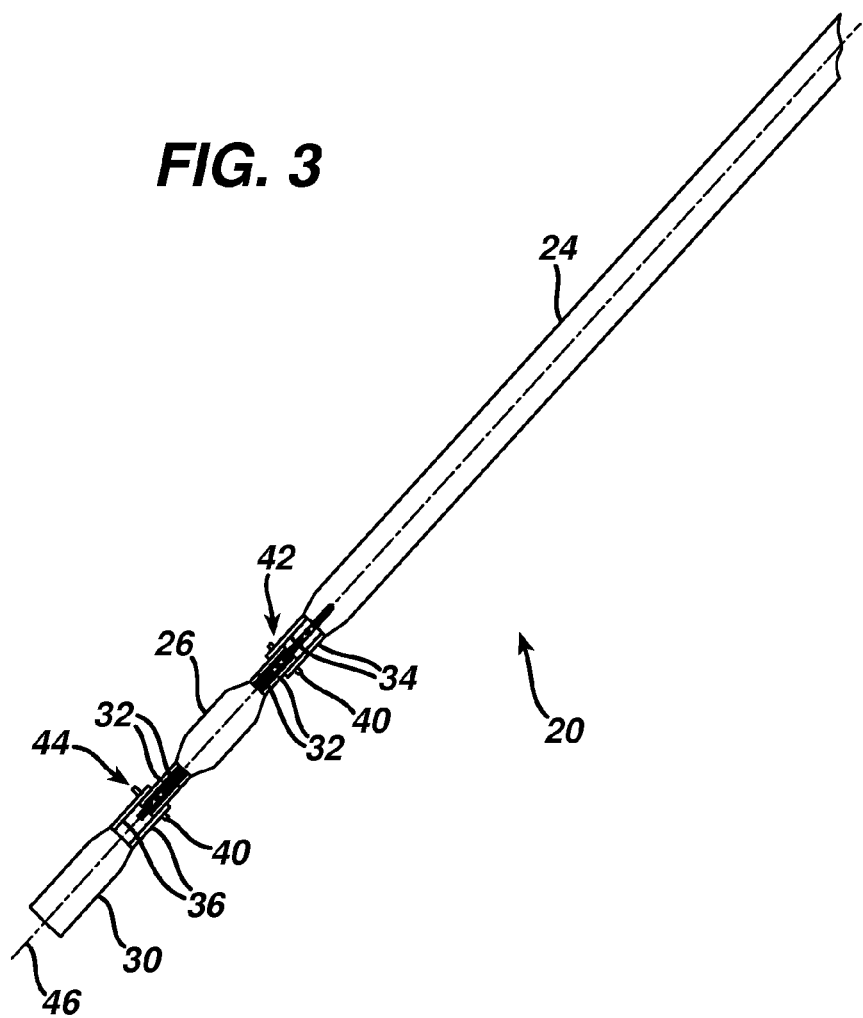
FIG. 3 is a perspective view of the distal end of the instrument shaft shown in a straight configuration.

As shown in greater detail in FIGS. 2 and 3, shaft 20 can have a plurality of sections along the longitudinal length of the shaft. In the embodiment shown, shaft 20 includes a primary (first) relatively proximal shaft section 24, a second (center) shaft section 26, third (end) shaft section 30. While three shaft sections are illustrated, it will be understood that more than three shaft sections may be employed in other embodiments.

First shaft section 24 can be a relatively rigid tubular section, and can have the longest length of the three sections 24, 26 and 30. In one embodiment, the third shaft section 30 can be longer than shaft section 26. Alternatively, shaft section 26 can be longer than shaft section 30, or the two shaft sections 36 and 30 could have substantially equal lengths.

In FIG. 1, first shaft section 24 is shown as extending distally from the handle in a generally straight line fashion. Alternatively, shaft section 24 can have a bend or curvature near its proximal end, such as is illustrated in FIG. 11. Such a bend or curvature can be helpful in preventing handles of two instruments from interfering one with the other when two or more instruments are inserted in closed spaced instrument openings or closely spaced trocars. A bend or curvature in the proximal portion of shaft section 24 may be fixed, or alternatively, may be in the form of a flexible "elbow" that can be adjusted, such as manually, at the point of use.

Figure 6:
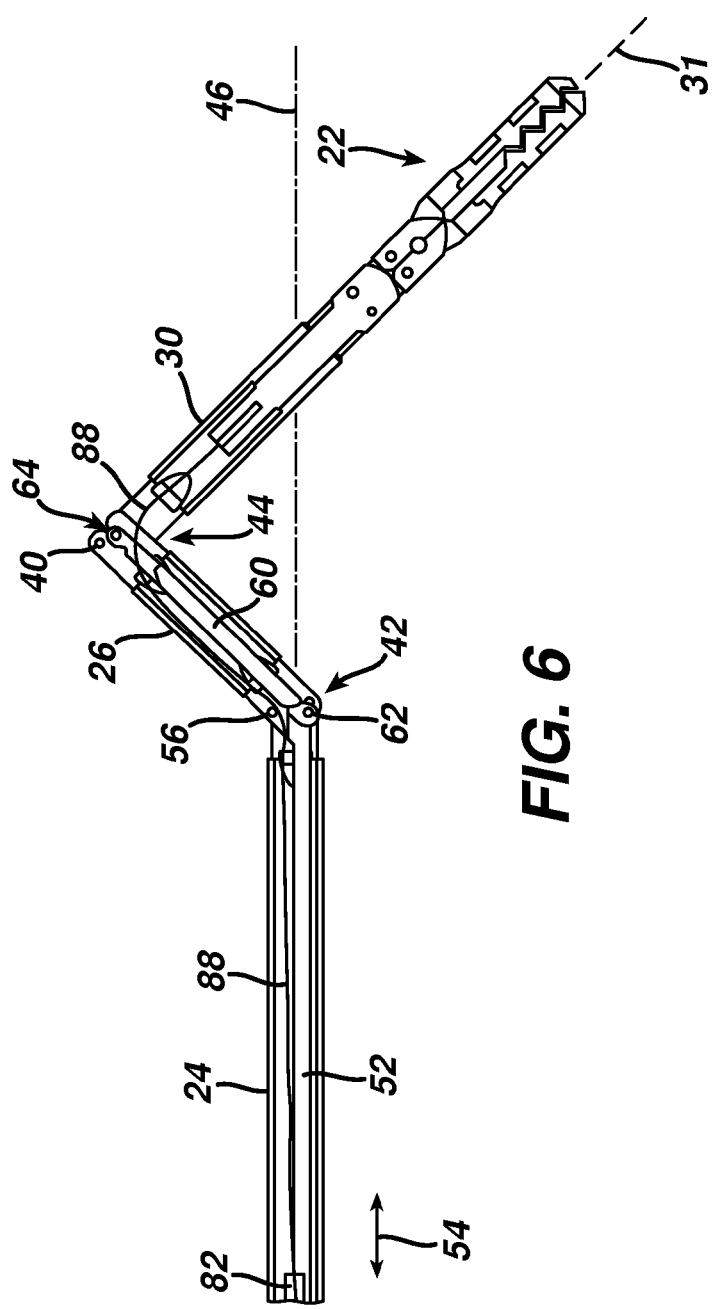
FIG. 6 is a sectional view of the distal end of the surgical instrument of FIG. 1, shown in an articulated configuration.

The proximal end of first section 24 may be connected to handle 12 so as to be rotatable relative to the handle about the longitudinal shaft axis. Referring to FIGS. 2 and 6, near the distal end of shaft 20, second, center section 26 and the distal most (third) shaft section 30 are connected in a pivotal relationship, such that center section 26 may be rotated relative to section 24 (such as about an axis generally perpendicular to the longitudinal axis of shaft section 24, for example an axis extending generally perpendicular to and out of the plane of FIG. 6), and third shaft section 30 may be rotated relative to section 26 (and relative to section 24) in a generally opposite direction.

Figure 4:
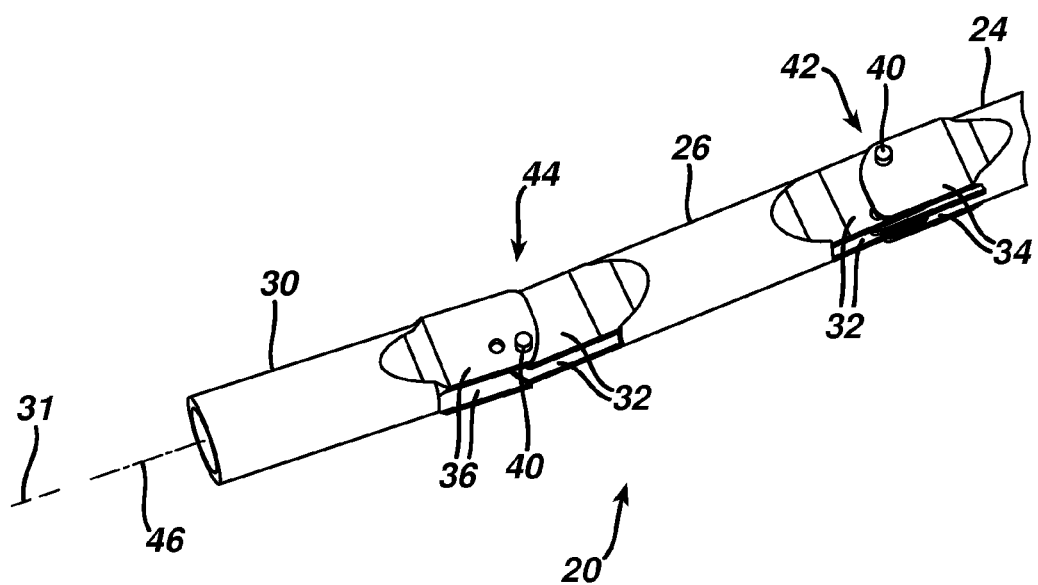
FIG. 4 is a more detailed, distal end view of the instrument shaft shown in FIG. 3.

The distal end of primary section 24 may be attached to the proximal end of center section 26, while the distal end of the second, center section 26 may be connected to the proximal end of third, distal most shaft section 30. End effector 22 is shown connected to the distal end of end section 30, and preferably rotates relative to the section 30 about a longitudinal axis of section 30. In FIG. 4, the longitudinal axis of section 30 is generally aligned with axis 46 when the shaft sections are aligned in a generally straight line configuration. In FIG. 6, the longitudinal axis of section 30 and working end 22 is denoted as axis 31, and is shown inclined with respect to axis 46.

As shown in FIGS. 3 and 4, the adjoining ends of shaft sections 24, 26 and 30 are shaped to include pairs of spaced arms, clevises, or similar structure for forming pivot connections/joints between the adjacent sections 24/26 and 26/30. The gap between arm pairs 32 on center section 26 can be less than the gap between arm pairs 34, 36 on primary and end sections 24, 30 respectively, to allow the center section arms to be inserted between the primary and end section arms. Pins 40 are shown inserted (eg. By press fit) through holes in each set of nested arm pairs to form pivot hinge-type joints 42, 44 between the adjacent shaft sections.

As shown in FIG. 4, the pins 40 and associated pivot connections/joints 42, 44 can be laterally/radially offset from the longitudinal centerline 46 of the shaft. In the embodiment shown, the pins 40 and associated pivot connections/joints are preferably spaced from the centerline of the shaft segments and positioned near the outer edge of the shaft sections. The proximal pivot joint 42 (between the primary and center sections 24, 26) is shown offset on the opposite side of the shaft centerline from the distal joint 44 (between the center and end sections 26, 30). Without being limited by theory, it is believed such an arrangement can be advantageous to allow the second, center section 26 and the third, end section 30 to pivot in opposite directions, as illustrated in FIGS. 2 and 6. Such an arrangement can also facilitate rotation of the distal portion of second section 26 away from the shaft axis 46, and rotation of the distal portion of the third section 30 back toward the shaft axis 46. As shown in FIG. 6, such an arrangement can permit the working end 22 (and also the distal portion of third section 30) to "cross" the axis 46. In the embodiment illustrated in FIG. 6, the working end 22 can be positioned at or near the axis 46, or across the axis 46, with the axis 31 of section 30 and working end 22 inclined with respect to the axis 46, as shown in FIG. 6.

FIGS. 5, 6, 7, and 7A illustrate the instrument 10 may include an assembly comprising a four bar linkage mechanism for providing pivoting center section 26 relative to primary and end sections 24, 30. The four bar linkage may include at least a portion of shaft section 26, at least a portion of shaft section 30, at least a portion of a relatively rigid first link 52, and at least a portion of a second link 60. At least a portion of link 52 can extend through at least a portion of shaft section 24, and at least a portion of second link 60 can extend through at least a portion of shaft section 26.

Figure 7:
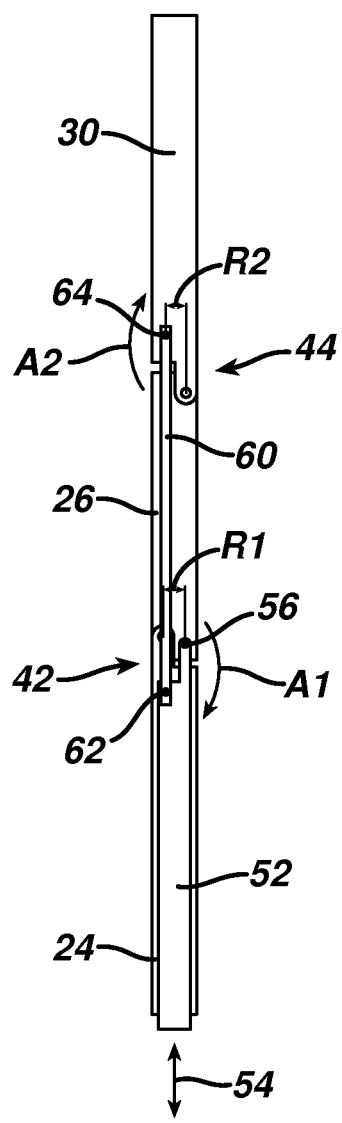
FIG. 7 is a diagrammatic view of the shaft sections, linkage and pivot connections shown in a straight configuration.
Figure 7A:
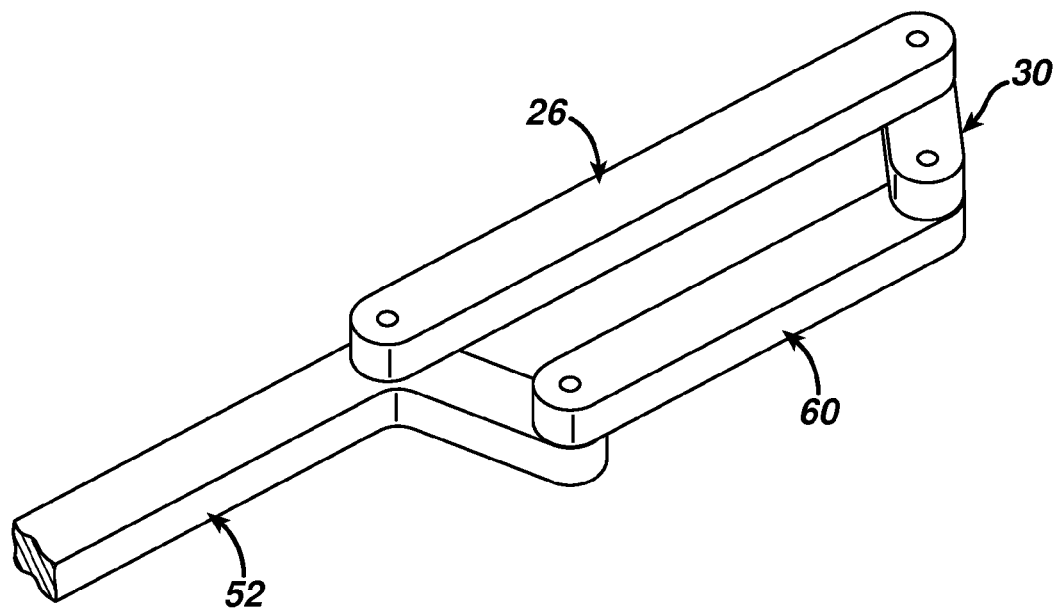
FIG. 7A is a schematic illustration showing an assembly comprising a four bar linkage mechanism where at least a portion of a second shaft segment and at least a portion of a third shaft segment serve as link members.

FIG. 7A provides a schematic illustration of the configuration of such a four bar linkage, comprising at least a portion of sections 24 and 30 and links 52 and 60. In FIG. 7A, portions of elements 24, 30, 52, and 60 are represented as simple link components for purpose of simplified illustration.

Figure 5:
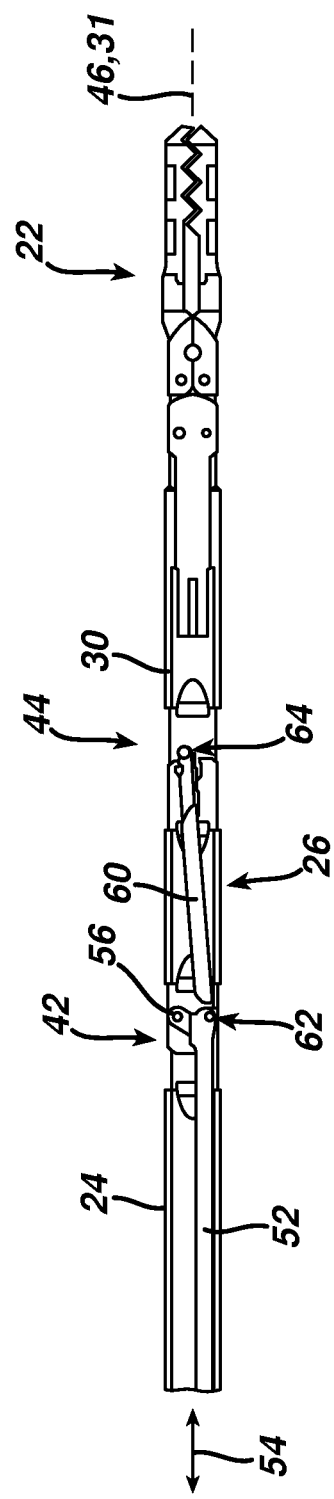
FIG. 5 is a sectional view of the distal end of the surgical instrument of FIG. 1, shown in a straight configuration.

Referring to FIGS. 5-7, first link 52 may disposed at partially within shaft section 24, and can include a proximal end operatively associated with a driving mechanism in handle 12. Arrow 54 in FIGS. 5 and 6 illustrates force/motion imparted to link 52 by the drive mechanism in handle 12. The distal portion of first link 52 can include a "dog leg" shape. The "heel" of the distal portion of first link 52 can be pivotably connected to the proximal portion of second (center) shaft section 26 at a pivot connection/joint 56.

The pivot connection/joint 56 between first link 52 and proximal end of center section 26 can be positioned on the opposite side of the shaft longitudinal centerline from the pivot connection 42 between the primary shaft section 24 and center shaft section 26. The "toe" of the distal end of first link 52 can be pivotally attached to the proximal end of the second relatively rigid link 60, as indicated at pivot connection/joint 62. In turn, the distal end of second link 60 can be pivotally connected to a proximal portion of third shaft section 30 at a pivot connection/point indicated at 64.

The pivot connection/joints can be provided with a pin inserted through the respective parts to allow the parts to pivot relative to each other. The linkage formed in part by first and second links 52, 60 enables joints 42, 44 to be substantially simultaneously actuated by a proximal pulling force on the first link 52 (by actuator in handle) to articulate the shaft 20 into a triangulated position, as shown in FIG. 6. In this position, a compound angle is formed by the separate shaft sections, with the axes of the shaft sections lying in separate, intersecting planes that extend perpendicularly out of the plane of FIG. 6. The axes of the shaft sections also lie within a common plane generally parallel to the plane of FIG. 6.

The compound angle in shaft 20 enables end effector 22 to approach a surgical site in a non-linear position relative to the primary shaft section 24. The degree of the compound angle formed by the pivoting shaft sections can be varied by varying the pulling force/displacement on first link 52. Varying the size of the compound angle changes the direction of approach of end effector 22 to the surgical site, which can assist in allowing for more precise positioning of the end effector.

Figure 8:
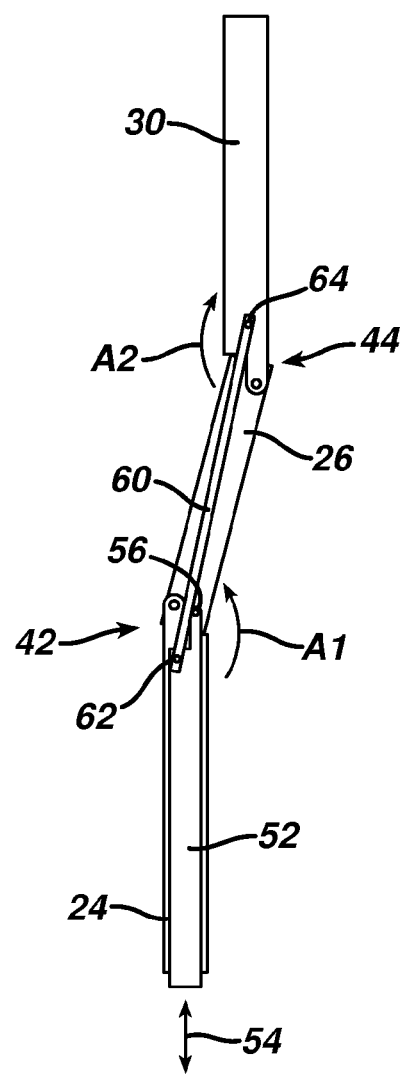
FIG. 8 is a diagrammatic view of the shaft sections, linkage and pivot connections shown in a representative articulated configuration.
Figure 9:
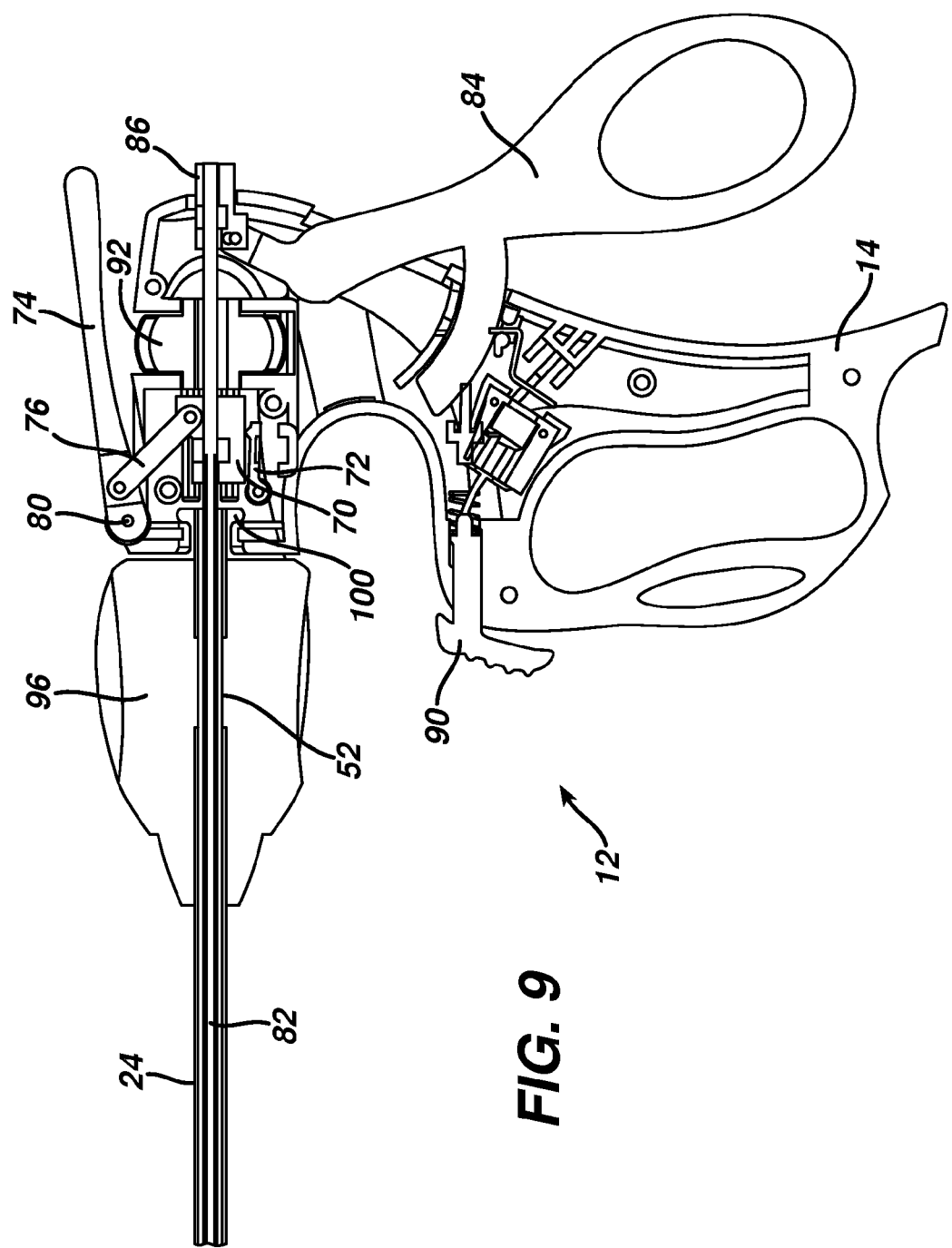
FIG. 9 is a sectional view of an exemplary handle including controls for articulating the instrument shaft.
Figure 10:
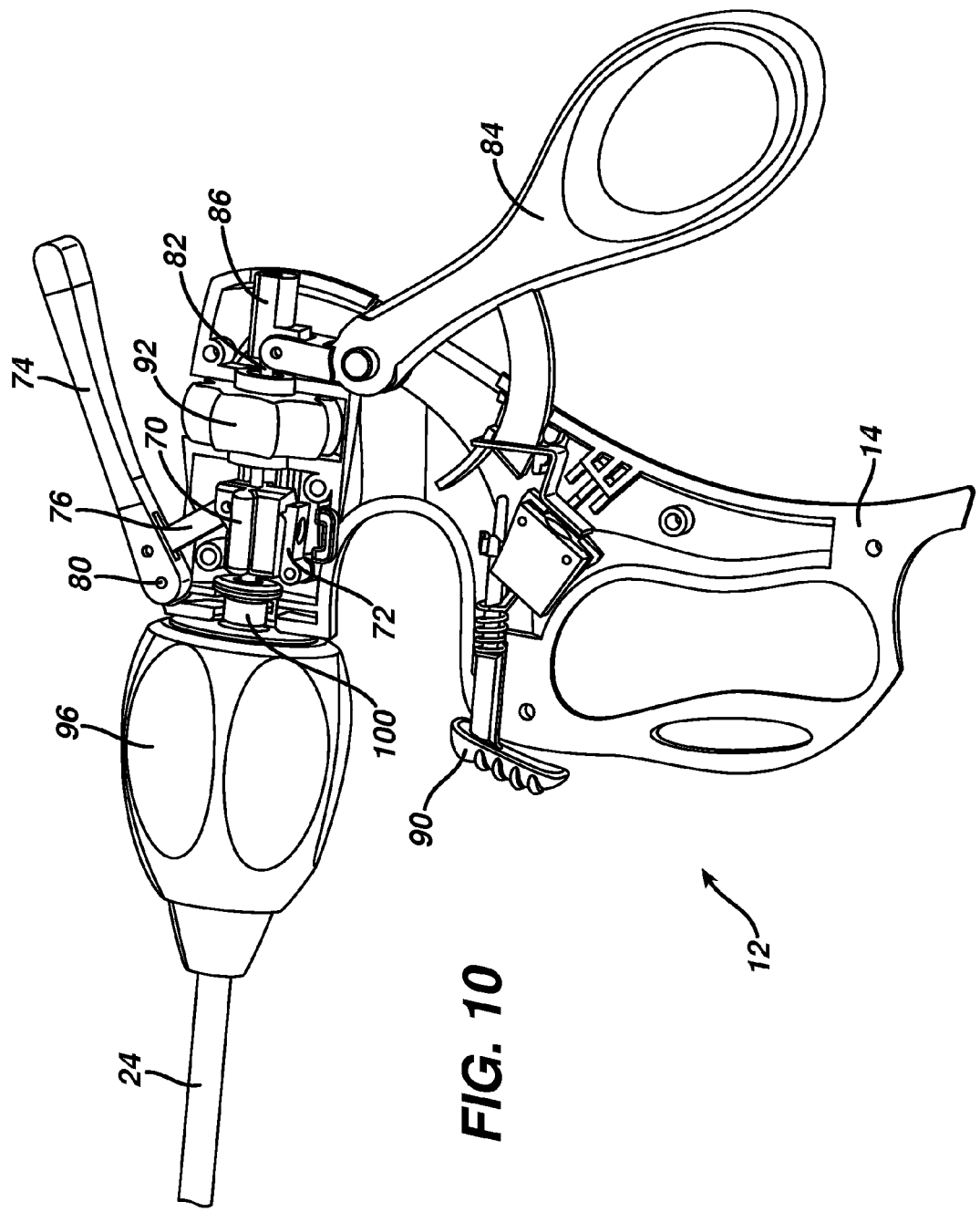
FIG. 10 is a perspective view of the handle of FIG. 9, shown with the handle cover removed.

FIGS. 7 and 8 illustrate in greater detail the compound angle formed by shaft sections 24, 26 and 30, as well as the movement of the first and second links 52, 60 as the shaft sections pivot about joints 42, 44. As shown in FIG. 7, the pivot connection between first link 52 and center section 26 is spaced from the pivot connection between primary and center sections 24, 26 by a distance labeled R1. Likewise, the pivot connection 64 between second link 60 and end section 30 is spaced from the pivot connection between the center and end shaft sections 26, 30 by a distance labeled R2. As first link 52 is pulled proximally by a driving force in handle 12, the link in turn pulls proximally on second link 60. As the links are pulled proximally, the links apply a pulling force on center and end sections 26, 30. The opposing, off-center locations of the pivot points between the three shaft sections 24, 26 and 30, as well as the off-center and opposing locations of the pivot connections between the first and second links 52, 60 and center and end sections 26, 30, result in the sections pivoting/rotating in opposite directions, relative to the shaft centerline, in response to the pulling force of the links.

As shown in FIG. 8, the pivoting shaft sections 26, 30 form a pair of angles identified as angle A1 (between primary section 24 and center section 26) and angle A2 (between center section 26 and end section 30). The measure of angles A1 and A2 can be dependent, at least in part, upon the distances R1 and R2 between the respective pivot connections, with each of the angles A1, A2 being determined separately by the associated distance R1, R2. The desired range for the compound angle formed by A1 and A2 in one embodiment is determined by the distances R1 and R2, with the distance R2 (between the distal pivot connections) being less than or equal to the distance R1 (between the proximal pivot connections). In at least one embodiment, the ratio R1/R2 of the separation distances can be the same as the ratio A1/A2 of the angles. Angle A1 can preferably be in the range of 90°-180°, while angle A2 can preferably be in the range of 60°-180°. Each of the distances R1 and R2 between the respective pivot connections may be limited by the outside diameter of shaft sections 24, 26 and 30, though in alternative embodiments, extensions or tabs could be used to increase R1 and/or R2 beyond what would generally be considered the outside diameter of the shaft sections. In one embodiment, the values of R1 and R2 range between a minimum of (0.5×diameter) and a maximum of (0.85×diameter) of the respective shaft section at the designated pivot point.

As mentioned above, instrument 10 includes a handle 12 having controls for articulating shaft 20 as well as operating end effector 22. In the exemplary handle shown in FIGS. 9 and 10, first link 52 is shaped as a rigid tube having a proximal end attached to a driving mechanism in the handle. The driving mechanism includes a carriage 70 having a toothed surface in contact with a pawl 72. A lever 74 extends from the surface of handle 12 and can be manually operated by the surgeon as the surgeon grips the handle. A rod 76 connects the distal end of lever 74 to carriage 70. Lever 74 pivots about a pin 80 connected at a distal end. The pivoting of lever 74 is conveyed through rod 76 to carriage 70 to translate the carriage (and thus link 52) proximally and distally inside the handle. As carriage 70 translates, pawl 72 engages the ridges of the toothed surface to hold the position of first link 52 (and thus the angle of the articulated shaft) between actuations of lever 74. As lever 74 pivots downward, carriage 70 pulls first link 52 proximally within handle 12, causing the first and second links 52, 60 to articulate the distal end of shaft 20 into a triangulated configuration. As lever 74 pivots upward, carriage 70 pushes first link 52 distally, in turn pushing second link 60 distally through connection 62, straightening sections 26, 30 of shaft 20 into a linear configuration. As an alternative to lever 74 and carriage 70, other types of controls could be included within handle 12 for applying force to first link 52 in the direction of the shaft axis to articulate (and/or straighten) the distal shaft end.

A second driving mechanism may be included in handle 12 for operating end effector 22. This second driving mechanism can include a translating element extending from handle 12, distally through shaft 20, to end effector 22. The translating element includes a wire rod 82 having a proximal end attached to an activating member in the handle. The activating member includes a ratchet 86 which is driven by a thumb trigger 84. Ratchet 86 translates rod 82 along the longitudinal axis of shaft 20 in response to manual pressure on trigger 84. As trigger 84 is pivoted relative to the handle case, the trigger ratchets rod 82 proximally or distally through link 52. The translating element includes a flexible segment 88 (shown in FIG. 6) connected to rod 82 proximal of the pivot and end shaft sections 26 and 30. Flexible segment 88 is comprised of a pliable material such as, for example, nitinol, which is crimped onto the distal end of rod 82. The flexible segment continues distally through the articulating region of shaft 20 to end effector 22. The distal, flexible segment of the translating element is connected to end effector 22 to alter the condition of the effector, such as opening and closing the tissue grasper jaws, in response to translation of rod 82. The flexible extension of rod 82 through the articulating region of shaft 20 provides for control of the working instrument tip, yet allows for the articulation of the shaft at pivot joints 42, 44. The flexible extension also allows the end effector to be rotated through the articulated shaft.

A button 90 can be included on handle 12 for closing and holding the position of thumb trigger 84 to maintain the end effector in a particular state. A control, such as a knob 92, is also included in handle 12 for rotating the end effector 22. Knob 92 can rotate rod 82 a full 360° to in turn rotate the end effector (tissue grasper) a full revolution. An additional control, such as a second knob 96, is also provided on handle 12 for rotating shaft 20 a full 360° about the longitudinal shaft axis. The proximal end of shaft 20 is connected within knob 96 for rotating the shaft. A bushing 100 surrounds link 52 distal of carriage 70 for rotating the link relative to the carriage. Knobs 92, 96 allow for separate, relative rotation between the shaft and end effector. Shaft 20 can be rotated while articulated at joints 42, 44 to further increase the positioning range of the end effector.

Turning now to FIG. 11, which depicts a laparoscopic procedure using a single incision, multiple device access port device 102. Port device 102 can be inserted through a small incision in the abdominal cavity, such as at the navel, to provide access for a laparoscope 104 and the surgical instruments to the operative site. Port device 102 can include multiple instrument openings, each having an associated valve assembly. In FIG. 11, a pair of surgical instruments 10 as well as a laparoscope 104 (for visualization) are shown inserted through the device 102 into the surgical site.

Additional details regarding suitable single incision, multiple device access ports can be found in the following copending patent applications incorporated by reference in their entirety herein: U.S. patent application Ser. No. 12/399,482 entitled "Methods And Devices For Providing Access Into A Body Cavity" filed Mar. 6, 2009, U.S. patent application Ser. No. 12/399,473 entitled "Methods And Devices For Providing Access Into A Body Cavity" filed Mar. 6, 2009, U.S. patent application Ser. No. 12/512,542 entitled "Methods And Devices For Providing Access Into A Body Cavity" filed Jul. 30, 2009, and U.S. patent application Ser. No. 12/512,568 entitled "Methods And Devices For Providing Access Into A Body Cavity" filed Jul. 30, 2009.

Figure 12:
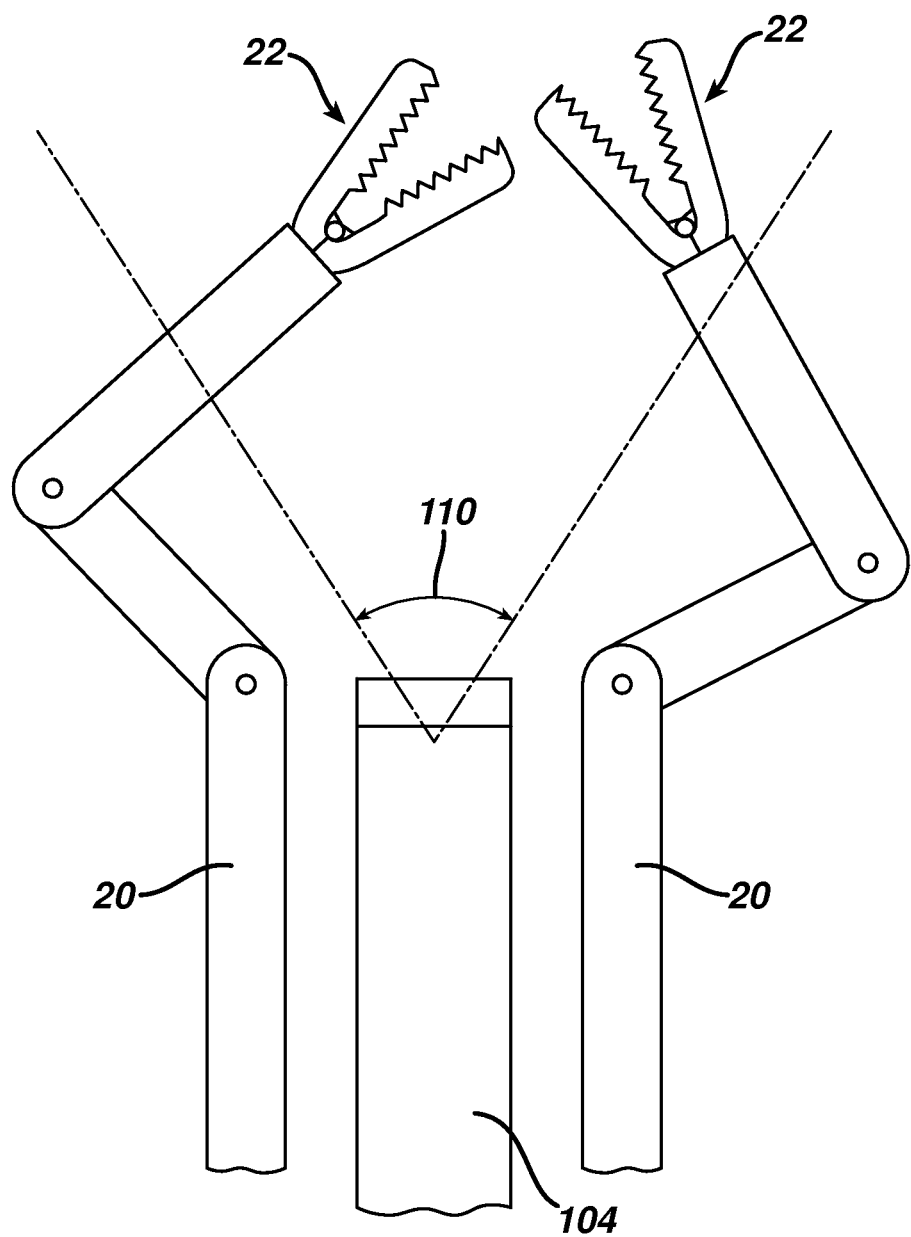
FIG. 12 is a schematic illustration of a laparoscopic surgical site illustrating instruments such as those shown in FIG. 11, where the instrument shafts are articulated to have a compound shaft angle and a triangular configuration, and where each instrument shaft includes a shaft segment rotated away from a field of view provided by a laparoscope, and where each instrument shaft has a more distal shaft segment and associated end effector rotated toward the field of view.

The instruments can be inserted through port device 102 into the body cavity in an initial, straight shaft configuration. After insertion, the instruments can be manipulated to bring the end effectors together in a non-interfering, cooperative relationship as shown in FIGS. 11 and 12.

The shafts 20 of each instrument can be articulated and rotated, in the manner described above, as necessary to reach the surgical site. The articulation angle of each shaft can be varied in increments using levers 74. As the shafts are articulated, the shafts can be simultaneously rotated via the handles 12 to draw the end effectors 22 together. The instrument shafts 20 can be triangulated and rotated to bring the end effectors 22 together at the surgical site, and position the end effectors within the viewing angle 110 of the laparoscope 104 as shown in FIG. 12.

FIGS. 13A and 13B show an alternative embodiment for articulating the distal end of the instrument shaft 20. In this embodiment, shaft 20 is divided into three tubular sections 24, 26 and 30, with pivot connections 112, 114 between the sections being offset from the shaft centerline 46 and positioned near the outer edges of the tube. The four bar linkage of the first embodiment is replaced with a single flexible member 116 that extends through the interior of the sections, to a connection point indicated at 120 in the distal, end section 30. In this embodiment, shaft 20 is articulated into a compound angle by applying a proximally directed pulling force to element 116, as indicated by arrow 122. The pulling force of element 116 on end section 30 pivots the section relative to center section 26 at connection point 114, which in turn pivots the center section relative to primary section 24 about pivot connection 112, producing compound angles A1 and A2, as shown in FIG. 13B. To straighten shaft 20, the pulling force on element 116 is released, allowing the element to slack and release the pivoting force on shaft sections 26, 30. As the tension in element 116 is released, shaft sections 26 and 30 will return to a substantially straight configuration. Flexible member 116 can comprise a tension cable or, alternatively, the member can be formed of a electroactive polymer, shape memory polymer or nitinol wire. Using the polymers, energy can be provided to the member to reduce the size of the member, thereby causing the member to pull proximally on end section 30 to pivot the sections. Using a nitinol wire, the wire can be activated to contract, applying a proximally directed force to end section 30. As the activating energy is removed, the nitinol wire will return to its original condition, causing the shaft sections 26, 30 to return to the straight configuration of FIG. 13A.

FIGS. 14A through 14C show a third alternative embodiment for articulating the instrument shaft 20, in which a pair of flexible members 116, 124 are alternatively pulled proximally to pivot sections 26, 30 of the shaft. Flexible members 116, 124 extend through the interior of the tubular shaft 20 and are connected to opposing inner surfaces of end section 30, as indicated at 130, 132. Applying a proximal pulling force, indicated by arrow 122, to one of the flexible members 116 causes the member to pull down on one side of end section 30, pivoting the section relative to center section 26 at connection 114. As end section 30 pivots down, the center section 26 is in turn pivoted in the opposite direction relative to primary section 24 at connection 116. The opposing pivot directions of end section 30 and center section 26 form the compound angle A1, A2. To return shaft 20 to a straight configuration, the proximal pulling forces on flexible members 116 and 124 are switched, with a pulling force, indicated by arrow 134, being applied to the opposite member 124. The pulling force of member 124 on the opposite side of end section 30 pivots the end section and, correspondingly, center section 26, back to a straight configuration.

Figure 15A:
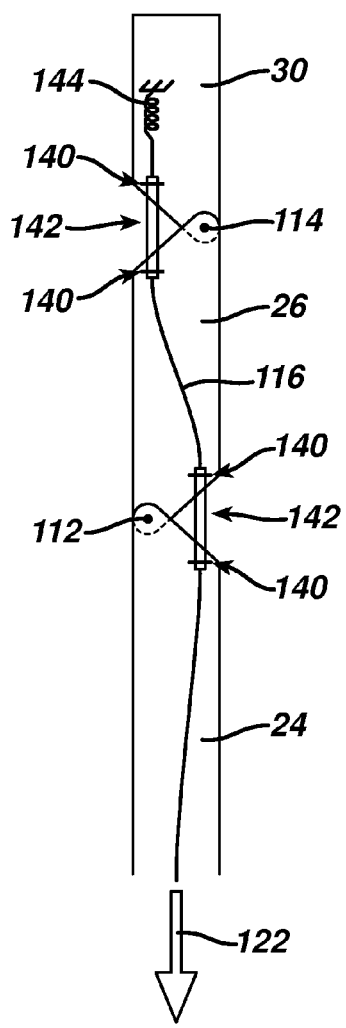
FIGS. 15A and 15B are schematic diagrams of the distal end of an instrument shaft showing a locking arrangement for the second articulating shaft embodiment.
Figure 15B:
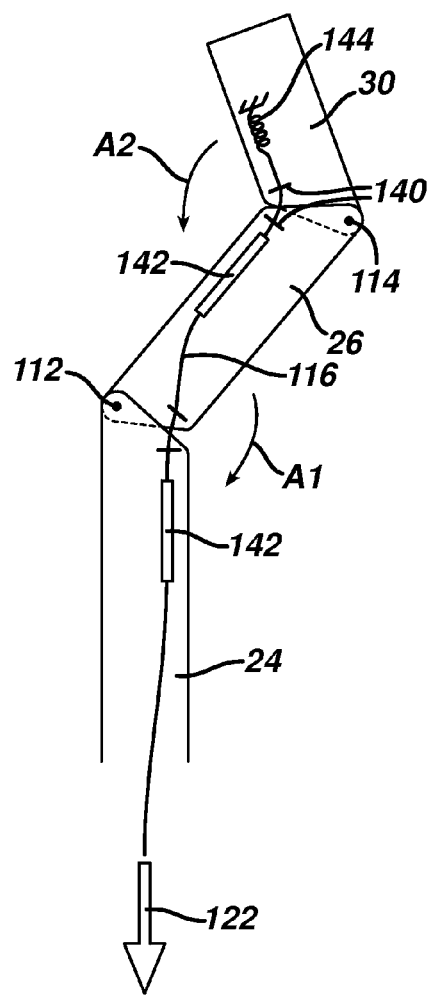

FIGS. 15A and 15B illustrate an alternative locking arrangement for the single flexible member embodiment shown in FIGS. 13A and 13B. This arrangement provides for locking shaft 20 in a straight configuration in the absence of a proximal pulling force on member 116. The locking arrangement is applicable when element 116 is a tension cable. In this arrangement, pairs of guide rings 140 are connected to the inner edge of shaft 20 on the side opposite each of the pivot connections 112, 114. A guide ring 140 is connected to each of the shaft sections at the pivot joint. Pins 142 are attached along the length of cable 116, with the pins having a diameter to fit within guide rings 140 and a length longer that the longitudinal distance between each pair of rings. Pins 142 are positioned along cable 116 so as to reside within guide rings 140 when the cable is in a non-tensioned state. A spring 144 is attached to the inside of shaft 20 adjacent the shaft distal end for biasing element 116 and pins 142 distally. As a proximal pulling force (indicated by arrow 122) is applied to cable 116, the movement of the cable pulls pins 142 from between guide rings 140. Releasing pins 142 from guide rings 140 allows shaft sections 26 and 30 to pivot in response to the pulling force of cable 116. When the proximal pulling force 122 on cable 116 is released, spring 144 pulls cable 116 and pins 142 distally, causing the pins to lodge within the pairs of guide rings 140 to lock the pivot joints 42, 44 in a straight configuration.

Figure 16A:
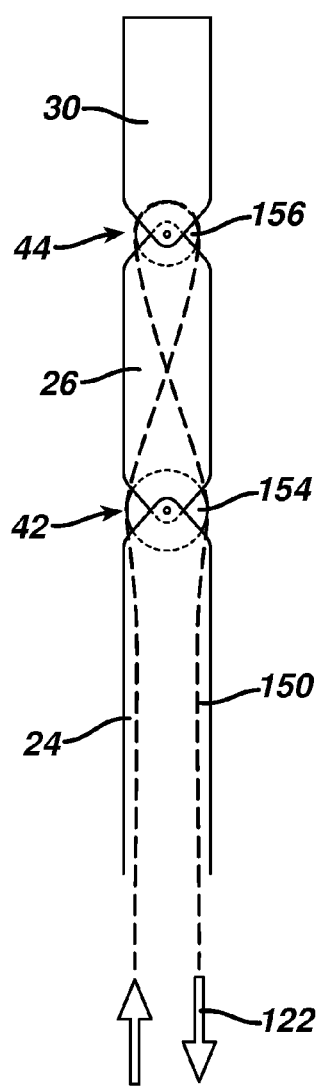
FIGS. 16A and 16B are schematic diagrams of the distal end of an instrument shaft showing a fourth embodiment for articulating the shaft.
Figure 16B:
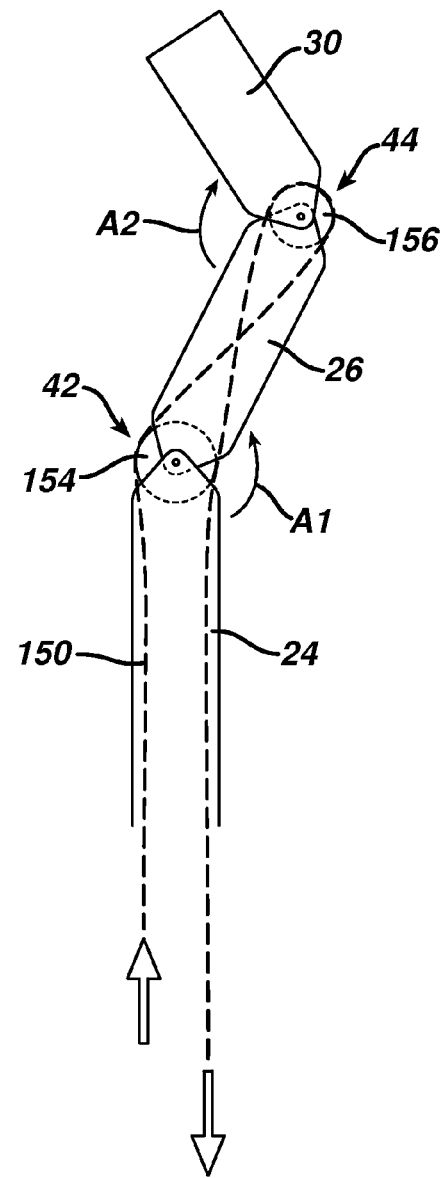

FIGS. 16A and 16B show a fourth embodiment for articulating an instrument shaft. In this embodiment, a flexible cable 150 is wrapped about a pair of pulleys 154, 156 to pivot shaft sections 26 and 30 at joints 42, 44. Pulleys 154, 156 are attached to the pivot connections between the shaft sections. The proximal pulley 154 has a larger diameter than the distal pulley 156. The ratio between the pulley diameters determines the ratio between the angles A1 and A2 of the compound shaft angle. The smaller diameter of distal pulley 156 causes the pulley to rotate at a higher velocity than the proximal pulley 154 in response to a proximal pulling force indicated by arrow 122. The higher rotation speed of pulley 156 pivots end section 30 relative to center section 26 at joint 44 at a faster rate than the pivoting of the center section 26 relative to the primary section 24 at joint 42. The difference in pivot rates results in the distal angle A2 being less than the proximal angle A1. As the proximal pulling force is removed, cable 150 retracts back about the pulleys 154, 156 returning shaft 20 to a straight configuration.

FIGS. 17A and 17B show a fifth embodiment for articulating an instrument shaft 20. In this embodiment, a rack and pinion is connected to each of the pivot joints 42, 44 between the shaft sections 24, 26 and 30. The proximal pinion 160 has a larger diameter than the distal pinion 162 to produce a proximal angle A1 that is larger than the distal angle A2. As a flexible member 150 is pulled proximally, as indicated by arrow 122, the flexible member pulls the attached racks 164 along the edges of the pinions 160, 162, rotating the pinions. The rotation of pinions 160, 162 in turn pivots the attached shaft sections 26, 30 at joints 42, 44, as shown in FIG. 17B. To return shaft 20 to a straight configuration, the flexible member 150 is allowed to retract, drawing the racks 164 back across pinions 160, 162 to rotate the pinions back in the opposite direction.

Figure 18A:
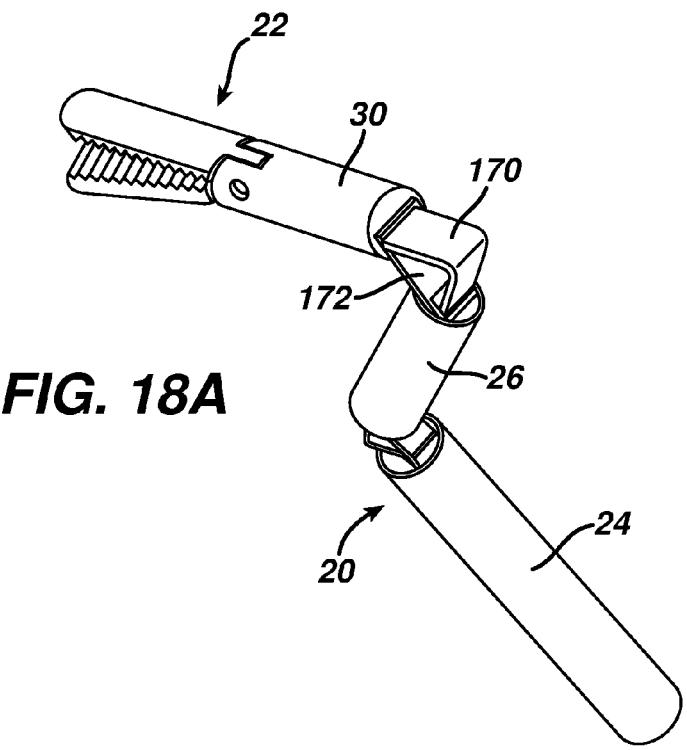
FIG. 18A is a perspective view of the distal end of the instrument shaft showing a sixth embodiment for articulating the shaft.
Figure 18B:
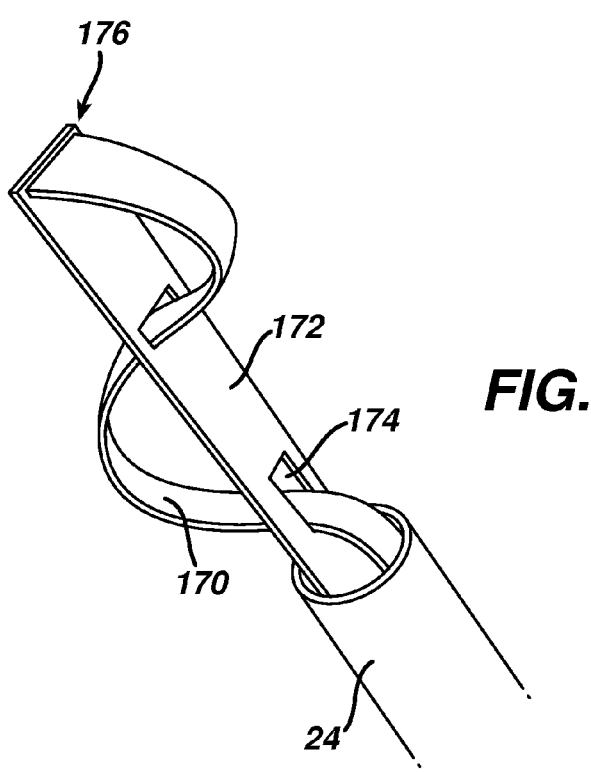
FIG. 18B is a more detailed perspective view of the interconnected bands of the sixth embodiment.

FIGS. 18A and 18B show a sixth embodiment for articulating an instrument shaft 20. In this embodiment, a pair of bands 170, 172 extend proximally through shaft 20 to the instrument handle (not shown). Bands 170 and 172 can be flexible or semi rigid. Bands 170, 172 are shown stacked together so as to allow relative sliding motion between the bands. Bands 170, 172 can be fixed together at the distal end of the shaft, as indicated at 176. Proximal of attachment point 176, bands 170, 172 are interconnected by threading a first one of the bands 170 through notches 174 in the second band 172, as shown in FIG. 18B. The distal, connected ends of the two bands are attached to the end effector 22. To move the end effector, the proximal end of the second band 172 is pulled proximally while the proximal end of the first band 170 is held fixed. The relative pulling motion between the bands causes the second band 172 to slide relative to the first band 170. The relative sliding motion between the bands causes the first band 170 to bow relative to the second band 172. Bands 170, 172 are constrained by the distal shaft sections 26, 30 such that the flexing movement of the bands articulates the shaft sections as shown in FIG. 18A, moving the position of the end effector 22.

FIGS. 19A and 19B show a seventh embodiment for articulating an instrument shaft. In this embodiment, pairs of magnets 180 are located at each of the pivot joints 42, 44 between the shaft sections 24, 26 and 30 to pivot the sections. The magnet pair at joint 42 is located on the opposite side of shaft 20 from the pair at joint 44 to pivot the sections in opposite directions relative to the longitudinal shaft axis. The magnet pairs 180 are oriented with opposite poles facing, so that the magnets are drawn towards each other to pivot the shaft sections. A movable overtube 182 extends over shaft 20. When overtube 182 is in a forward position, covering the length of shaft 20 as shown in FIG. 19A, the overtube forces the magnet pairs 180 apart, constraining shaft sections 24, 26 and 30 to a straight condition. When overtube 182 is retracted, as shown in FIG. 19B, the forces between magnet pairs 180 draw the magnets together, pivoting the shaft sections 24, 26 and 30 at joints 42, 44.

Figure 20:
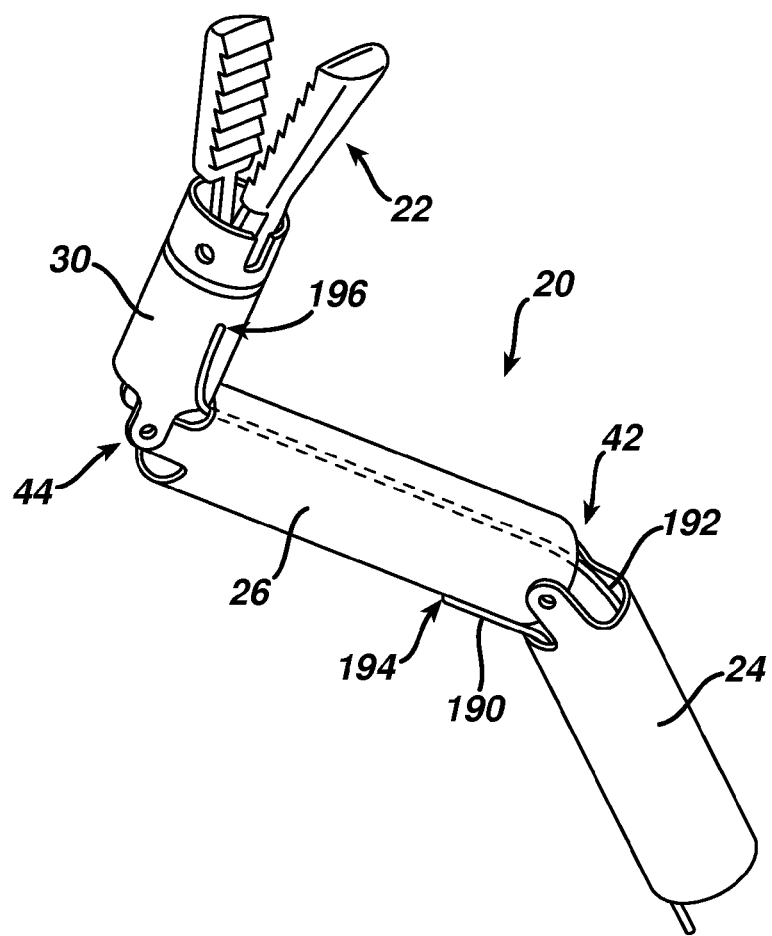
FIG. 20 is a perspective view of an eighth embodiment for articulating an instrument shaft.

FIG. 20 shows another alternative embodiment for articulating an instrument shaft, in which a pair of flexible linkages, such as cables 190, 192, extends longitudinally through shaft sections 24, 26 and 30. The distal end of a first one of the cables 190 is attached to center shaft section 26, as shown at 194, while the distal end of the second cable 192 is attached to the end shaft section 30, as shown at 196. The distal ends of cables 190, 192 are attached to opposite sides of the shaft 20, with first cable 190 attached to the outer surface of the shaft and second cable 192 attached to the inner surface of the shaft. Shaft sections 24, 26 and 30 are connected together by hinge joints 42, 44. To articulate shaft 20, proximally directed pulling forces are applied to the proximal ends of cables 190, 192 by driving mechanisms within handle 12 (not shown). These pulling forces are transferred through cables 190, 192 to the respective shaft sections 26, 30. As the cables 190, 192 exert a pulling force on sections 26, 30 the sections pivot about joints 42, 44 as shown. Shaft sections 26, 30 pivot in opposite directions relative to the shaft axis to form a compound angle, due to the opposing positions of the distal cable end connections. To return shaft 20 to a straight configuration, the pulling forces on cables 190, 192 are released, allowing the cables to slack and release the force on shaft sections 26, 30.

The foregoing description of embodiments of the invention has been presented for purposes of illustration and description. It is not intended to be exhaustive or to limit the invention to the precise form disclosed. Modifications or variations are possible in light of the teachings in the art. The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention not be limited by the specific embodiments described above.

What is claimed is:

1. A medical device comprising:
    an actuator comprising an articulation input and an actuation input;
    a shaft comprising
        a proximal shaft portion connected to the actuator, the proximal shaft portion defining a longitudinal centerline,
        a middle shaft portion connected to the proximal shaft portion by a single first pivot joint laterally offset on a first side from the longitudinal centerline of the proximal shaft portion and from a longitudinal centerline of the middle shaft portion, the first pivot joint connected to the articulation input such that the articulation input causes the middle shaft portion to articulate laterally away from the longitudinal centerline of the proximal shaft portion,
        a distal shaft portion connected to the middle shaft portion by a single second pivot joint laterally offset on a second side opposite the first side from the longitudinal centerline of the middle shaft portion and from a longitudinal centerline of the distal shaft portion, the second pivot joint connected to the articulation input such that the articulation input causes the distal shaft portion to articulate medially towards the longitudinal centerline of the proximal shaft portion; and
    an end effector connected to the distal shaft portion and operably connected to the actuation input.

2. The medical device of claim 1, wherein the end effector comprises a pair of jaws that open and close relative one another.

3. The medical device of claim 1, wherein the articulation input simultaneously articulates the middle shaft portion about the first pivot joint and the distal shaft portion about the second pivot joint.

4. The medical device of claim 1, further comprising a first link positioned in the proximal shaft portion, the first link connected to the articulation input and to the middle shaft portion.

5. The medical device of claim 4, further comprising a second link positioned in the middle shaft portion, the second link being connected to the first link and to the distal shaft portion.

6. The medical device of claim 1, further comprising a flexible articulation member positioned in the proximal and middle shaft portions, the flexible articulation member being connected to the articulation input and to the distal shaft portion.

7. A medical device comprising:
    an actuator comprising an articulation input and an actuation input;
    a shaft comprising a proximal shaft portion connected to the actuator, the proximal shaft portion defining a longitudinal axis, a middle shaft portion connected to the proximal shaft portion by a single first pivot joint on a first side of the longitudinal axis, and a distal shaft portion connected to the middle shaft portion by a single second pivot joint on a second side opposite the first side, wherein the first and second pivot joints are offset on opposite lateral sides of a longitudinal centerline of the middle shaft portion; and an articulation linkage connected to the shaft and the articulation input, the articulation linkage being operable to pivot the middle shaft portion about the first pivot joint such that the middle shaft portion articulates laterally away from the longitudinal axis, and simultaneously pivot the distal shaft portion about the second pivot joint such that the distal shaft portion articulates medially towards the longitudinal axis; and an end effector connected to distal shaft portion, the end effector being operably connected to the actuation input.

\* \* \* \* \*